United States Patent
Lupia et al.

(10) Patent No.: US 8,216,596 B2
(45) Date of Patent: *Jul. 10, 2012

(54) STABILIZED BODY CARE PRODUCTS, HOUSEHOLD PRODUCTS, TEXTILES AND FABRICS

(75) Inventors: Joseph A. Lupia, Reinach (CH); Joseph Suhadolnik, Yorktown Heights, NY (US); Mervin G. Wood, Maysville, KY (US); Wanda H. Martin, Fruitdale, AL (US)

(73) Assignee: BASF SE, Ludwigshafen (DE)

( * ) Notice: Subject to any disclaimer, the term of this patent is extended or adjusted under 35 U.S.C. 154(b) by 1693 days.

This patent is subject to a terminal disclaimer.

(21) Appl. No.: 11/432,006

(22) Filed: May 11, 2006

(65) Prior Publication Data

US 2006/0264345 A1    Nov. 23, 2006

Related U.S. Application Data

(60) Provisional application No. 60/682,233, filed on May 18, 2005.

(51) Int. Cl.
*A61K 8/02* (2006.01)

(52) U.S. Cl. ........ 424/401; 424/70.1; 510/119; 546/242

(58) Field of Classification Search ................ 424/70.1, 424/401; 546/242; 510/119
See application file for complete search history.

(56) References Cited

U.S. PATENT DOCUMENTS

| | | | |
|---|---|---|---|
| 6,254,724 B1 | 7/2001 | Seltzer et al. | 162/70 |
| 2005/0220727 A1 * | 10/2005 | Lupia et al. | 424/59 |
| 2006/0040836 A1 | 2/2006 | Lupia et al. | 510/130 |

FOREIGN PATENT DOCUMENTS

| | | |
|---|---|---|
| WO | 00/25730 | 5/2000 |
| WO | 00/25731 | 5/2000 |
| WO | 01/07550 | 2/2001 |
| WO | WO 03103622 A1 * | 12/2003 |
| WO | 2004/076419 | 9/2004 |
| WO | 2005/042828 | 5/2005 |
| WO | 2006/021526 | 3/2006 |

* cited by examiner

*Primary Examiner* — Gina C Yu
(74) *Attorney, Agent, or Firm* — Shelia A. Loggins

(57) ABSTRACT

Disclosed are stabilized body care products, household products, textiles and fabrics which comprise certain sterically hindered amine salt compounds. Dyed products and articles are effectively stabilized against color degradation. The products are for example skin-care products, hair-care products, dentifrices, cosmetics, laundry detergents and fabric softeners, non-detergent based fabric care products, household cleaners and textile-care products.

23 Claims, No Drawings ly alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

HY is an inorganic or organic acid; and, wherein the total charge of cations is equal to the total charge of anions; and BM is a basic material selected from the group consisting of alkali metal hydroxides, alkaline earth metal hydroxides, and amines.

STABILIZED BODY CARE PRODUCTS, HOUSEHOLD PRODUCTS, TEXTILES AND FABRICS

This application claims benefit under 35 USC 119(e) of U.S. provisional app. No. 60/682,233, filed May 18, 2005.

The present invention relates to the use of certain sterically hindered amine salt compounds for the protection of body care products, household products, textiles and fabrics against the deleterious effects of light, heat and oxygen.

The stabilized compositions for example comprise dyes that are stabilized against color change.

BACKGROUND

WO 00/25730 and WO 00/25731 are aimed at the stabilization of body care and household products.

U.S. Pat. app. No. 60/377,381, filed May 2, 2002, discloses the use of selected hindered nitroxyl, hydroxylamine and hydroxylamine salt compounds in formulations of body care products, household products, textiles and fabrics, and is incorporated herein by reference.

U.S. Pat. app. No. 60/603,590, filed Aug. 23, 2004, discloses the use of selected hindered nitroxyl, hydroxylamine and hydroxylamine salt compounds in formulations of body care products, household products, textiles and fabrics, and is incorporated herein by reference.

WO 01/07550 teaches the treatment of fabric with hindered amine stabilizers.

U.S. Pat. No. 6,254,724 teaches the stabilization of pulp and paper with hindered-amine based compounds.

It is now found that certain sterically hindered amine salt compounds provide outstanding protection against light-induced fading of home personal care products.

DETAILED DISCLOSURE

The present invention pertains to a stabilized composition comprising
(a) a body care product, household product, textile or fabric and
(b) an effective stabilizing amount of one or more compounds of formula (I)

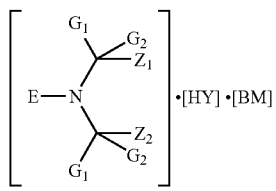

wherein $G_1$ and $G_2$ are independently alkyl of 1 to 4 carbon atoms or are together pentamethylene; $Z_1$ and $Z_2$ are each methyl, or $Z_1$ and $Z_2$ together form an unsubstituted linking moiety or a linking moiety substituted by one or more groups selected from an ester, ether, hydroxy, oxo, cyanohydrin, amide, amino, carboxy or an urethane group;

E is alkoxy of 1 to 18 carbon atoms, cycloalkoxy of 5 to 12 carbon atoms or aralkoxy of 7 to 15 carbon atoms, or E is —O-T-(OH)$_b$, T is a straight or branched chain alkylene of 1 to 18 carbon atoms, cycloalkylene of 5 to 18 carbon atoms, cycloalkenylene of 5 to 18 carbon atoms, a straight or branched chain Y is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, a carboxylate of hydroxyethylethylenediaminetriacetic acid, a carboxylate of ethylenediamine-tetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

Y is a carboxylate, especially a carboxylate of a mono-, di-, tri- or tetracarboxylic acid, mainly of 1-18 carbon atoms, such as a formate, acetate, benzoate, citrate, or oxalate.

For example, Y is chloride, bisulfate, sulfate, phosphate, nitrate, ascorbate, formate, acetate, benzoate, oxalate, citrate, a carboxylate of ethylenediaminetetraacetic acid or of diethylene-triaminepentaacetic acid or polyacrylate.

For instance, Y is chloride, bisulfate, ascorbate, or citrate.

Amines are defined as $R_{115}$—N($R_{116}$)—$R_{117}$, wherein $R_{115}$, $R_{116}$, and $R_{117}$ are independently hydrogen, straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{118}$, —O$R_{119}$, $R_1$, or —NH$_2$ groups or mixtures thereof; or said alkyl or said alkenyl interrupted by one or more —O—, —NH— or —NR$_{119}$— groups or mixtures thereof and which can be unsubstituted or substituted by one or more —OH, —OR$_{119}$ or —NH$_2$ groups or mixtures thereof;

$R_{118}$ is hydrogen, straight or branched chain $C_1$-$C_{18}$alkyl, $C_5$-$C_{12}$cycloalkyl, straight or branched chain $C_3$-$C_8$alkenyl, $C_6$-$C_{14}$aryl or $C_7$-$C_{15}$aralkyl, $R_{119}$ is straight or branched chain alkyl of 1 to 18 carbon atoms.

Amines are also bicyclic; for example, 1,4-diazabicyclo [2.2.2]octane.

The total charge for the salts of formula (I) is neutral. For example, the total number of cations is equal to the total number of anions.

Alkali metal hydroxide is sodium hydroxide, potassium hydroxide, or rubidium hydroxide.

For instance, the alkali metal hydroxide is sodium hydroxide or potassium hydroxide.

Alkaline earth metal hydroxide is magnesium hydroxide, calcium hydroxide, strontium hydroxide, or barium hydroxide.

For instance, the alkaline earth metal hydroxide is magnesium hydroxide or calcium hydroxide.

The certain hindered amine compounds described herein are acid salts of the corresponding hindered amine compounds.

For example, Z1 and Z2 together are a hydrocarbon linking moiety containing 1-200 carbon and heteroatoms; for instance, 1-60 carbon atoms and 0-60 heteroatoms; especially, 0-30 heteroatoms selected from oxygen atoms and nitrogen atoms.

For instance, Z1 and Z2 as a linking moiety are a chain of 2 or 3 carbon atoms or 1 or 2 carbon atoms and a nitrogen or oxygen atom forming together with the remaining structure in formula (I) a saturated unsubstituted 5- or 6-membered heterocyclic ring or a 5- or 6-membered heterocyclic ring substituted by one or more groups selected from an ester, ether, hydroxy, oxo, cyanohydrin, amide, amino, carboxy or an urethane group. The substituents in Z1 and Z2 themselves may contain hindered amine moieties. For example, the compounds of the formula (I) contain 1-4 hindered amine or hindered ammonium groups. For instance, the compounds of formula (I) contain 1 or 2 hindered amine or hindered ammonium moieties.

Any group denoted as aryl mainly means $C_6$-$C_{12}$aryl; for example, aryl is phenyl or naphthyl; for instance, aryl is phenyl.

Group denoted as alkyl are, within the definitions given, mainly $C_1$-$C_{18}$alkyl, for example methyl, ethyl, propyl such as n- or isopropyl, butyl such as n-, iso-, sec- and tert-butyl, pentyl, hexyl, heptyl, octyl, nonyl, decyl, undecyl, dodecyl, tridecyl, tetradecyl, pentadecyl, hexadecyl, heptadecyl, or octadecyl.

Groups denoted as alkylene are, within the definitions given, for example methylene, 1,2-ethylene, 1,1-ethylene, 1,3-propylene, 1,2-propylene, 1,1-propylene, 2,2-propylene, 1,4-butylene, 1,3-butylene, 1,2-butylene, 1,1-butylene, 2,2-butylene, 2,3-butylene, or —$C_5H_{10}$—, —$C_6H_{12}$—, $C_7H_{14}$, —$C_8H_{16}$—, —$C_9H_{18}$—, —$C_{10}H_{20}$—, —$C_{11}H_{22}$—, —$C_{12}H_{24}$—, —$C_{13}H_{26}$—, $C_{14}H_{28}$—, $C_{15}H_{30}$—, —$C_{16}H_{32}$—, —$C_{17}H_{34}$—, or —$C_{18}H_{36}$—.

Groups denoted as cycloalkyl or cycloalkoxy are mainly $C_5$-$C_{12}$cycloalkyl or $C_5$-$C_{12}$cycloalkoxy, the cycloalkyl part being, for example, cyclopentyl, cyclohexyl, cycloheptyl, cyclooctyl, cyclononyl, cyclodecyl, cycloundecyl, or cyclododecyl. Cycloalkenyl is mainly $C_5$-$C_{12}$cycloalkenyl including cyclopentenyl, cyclohexenyl, cycloheptenyl, cyclooctenyl, cyclononenyl, cyclodecenyl, cycloundecenyl, or cyclododecenyl.

Aralkyl or aralkoxy is, for example, phenylalkyl or phenylalkoxy, which is alkyl or alkoxy substituted by phenyl. Examples for phenylalkyl or phenylalkoxy are, within the definitions given, benzyl, benzyloxy, alpha-methylbenzyl, alpha-methylbenzyloxy, cumyl, or cumyloxy.

Alkenyl residues are mainly alkenyl of 2 to 18 carbon atoms; for example, allyl.

Alkynyl residues are mainly alkynyl of 2 to 12 carbon atoms; for example, propargyl.

A group denoted as acyl is mainly R(C═O)—, where R is an aliphatic or aromatic moiety.

An aliphatic or aromatic moiety, such as mentioned above or other definitions, mainly is an aliphatic or aromatic $C_1$-$C_{30}$hydrocarbon; examples are aryl, alkyl, cycloalkyl, alkenyl, cycloalkenyl, bicycloalkyl, bicycloalkenyl, and combinations of these groups.

Examples for acyl groups are alkanoyl of 2 to 12 carbon atoms, alkenoyl of 3 to 12 carbon atoms, or benzoyl.

Alkanoyl embraces, for example, formyl, acetyl, propionyl, butyryl, pentanoyl, oroctanoyl; for example, $C_2$-$C_8$alkanoyl; for instance, acetyl.

Alkenoyl residues are, for example, acryloyl, or methacryloyl.

The alkyl groups in the different substituents may be linear or branched.

Examples for alkenyl groups with 2 to 4 carbon atoms are ethenyl, propenyl, or butenyl. Examples for alkyl groups with 1 to 4 carbon atoms interrupted by one or two oxygen atoms are —$CH_2$—O—$CH_3$, —$CH_2$—$CH_2$—O—$CH_3$, —$CH_2$—$CH_2$—O—$CH_2$—$CH_3$, —$CH_2$—O—$CH_2$—$CH_2$—O—$CH_3$, or —$CH_2$—O—$CH_2$—O—$CH_3$.

Examples for hydroxy substituted alkyl groups with 2 to 6 carbon atoms are hydroxy ethyl, di-hydroxy ethyl, hydroxy propyl, di-hydroxy propyl, hydroxy butyl, hydroxy pentyl, or hydroxy hexyl.

Examples of especially suited compounds of component (b) formula (I) are selected from the group consisting of formulae A* to EE* and (III) to (IIIc):

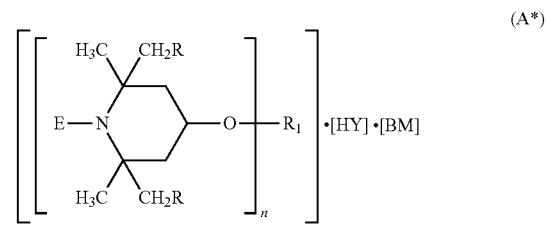

(A*)

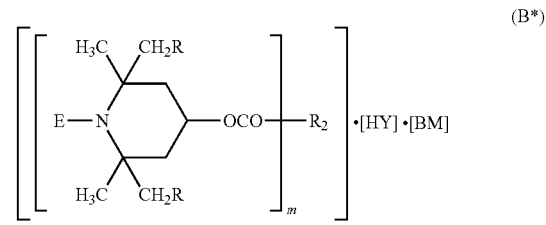

(B*)

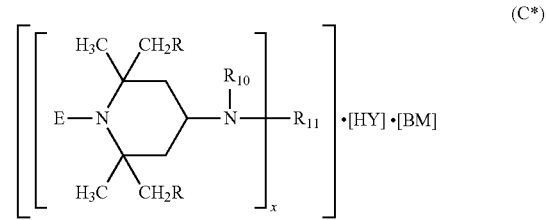

(C*)

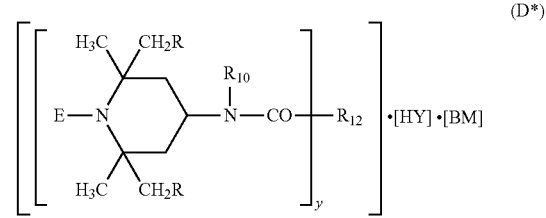

(D*)

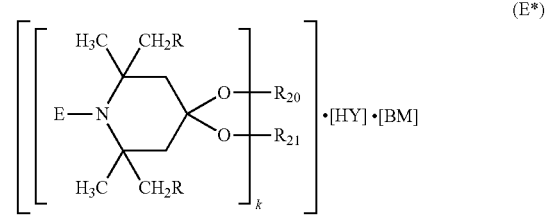

(E*)

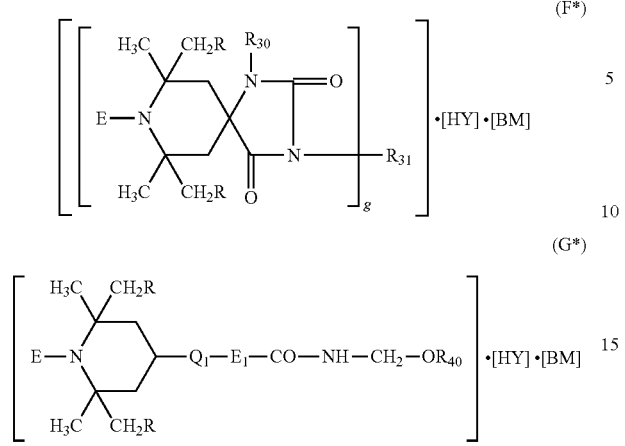 (F*)
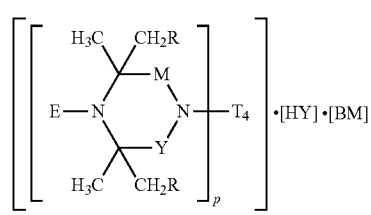 (G*)
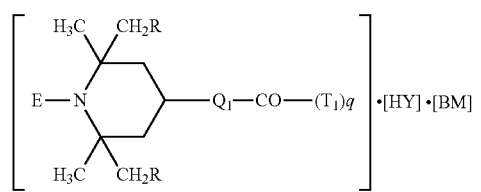 (H*)
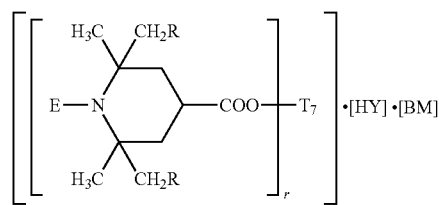 (I*)
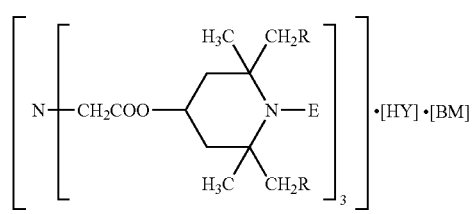 (J*)
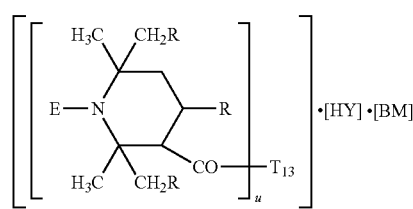 (K*)
(L*)
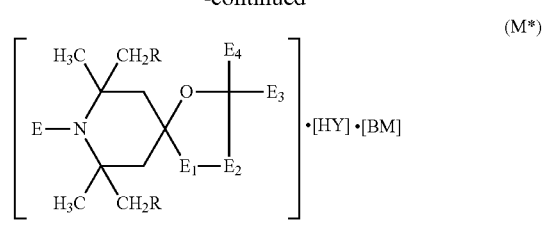 (M*)
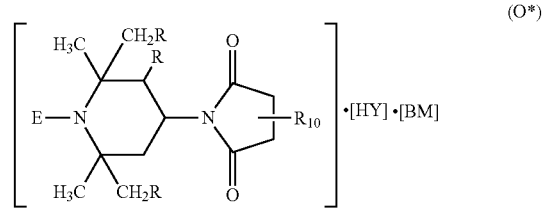 (O*)
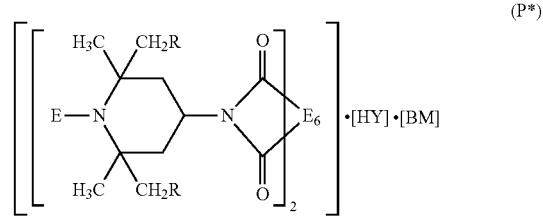 (P*)
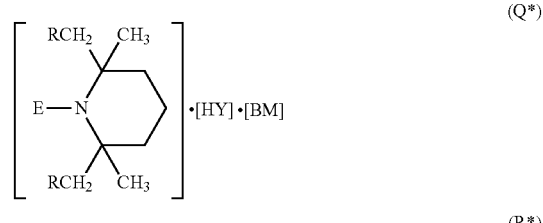 (Q*)
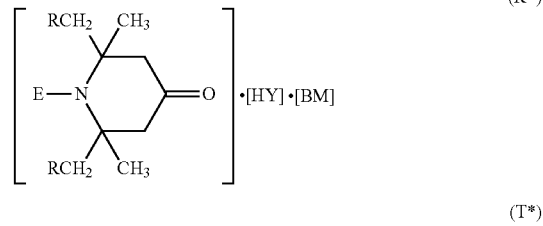 (R*)
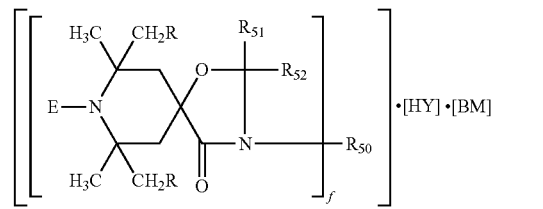 (T*)
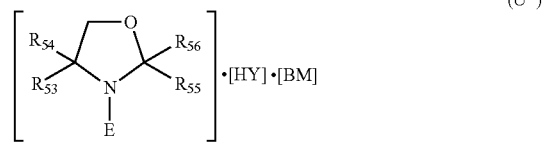 (U*)
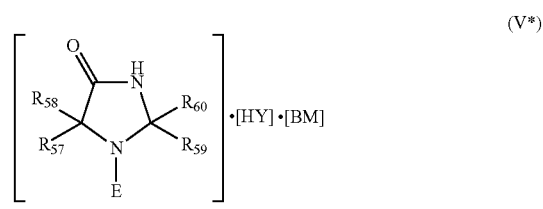 (V*)

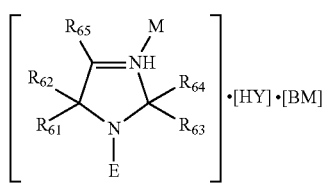(W*)

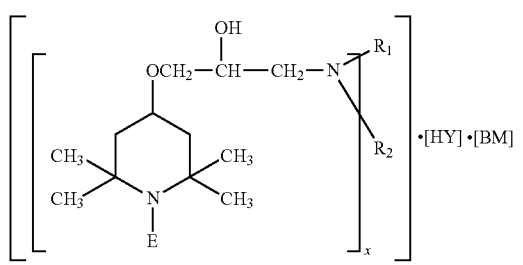(Y*)

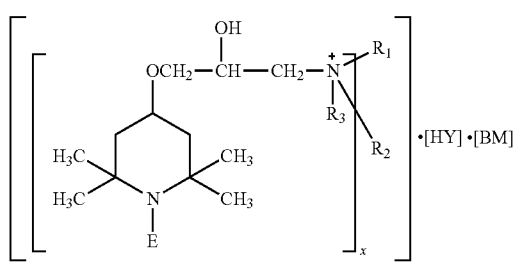(Z*)

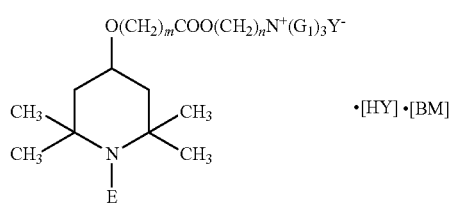(AA*)

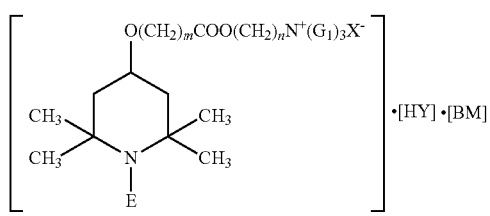(BB*)

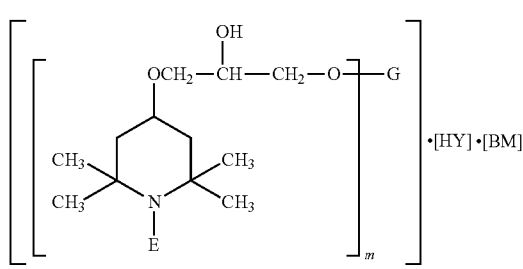(DD*)

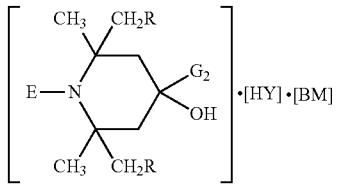(EE*)

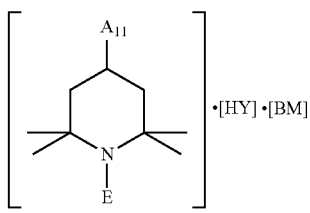(III)

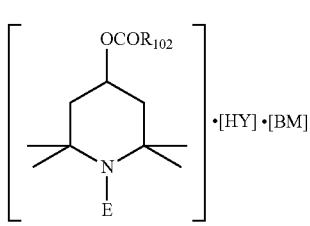(IIIa)

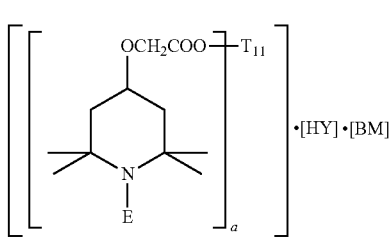(IIIb)

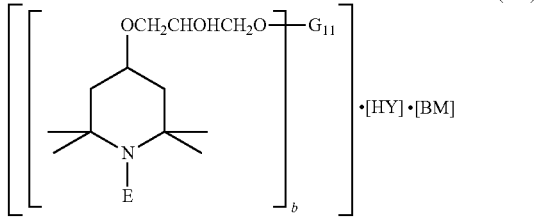(IIIc)

wherein

E is alkoxy of 1 to 18 carbon atoms, cycloalkoxy of 5 to 12 carbon atoms or aralkoxy of 7 to 15 carbon atoms, or E is $-O-T-(OH)_b$, T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen or methyl; and in formula (A*) n is 1 or 2, when n is 1, $R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where R$_2$ is alkyl of 1 to 8 carbon atoms or benzyl, when n is 2, $R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups;

in formula (B*), m is 1 to 4, and when m is 1, $R_2$ is alkyl of 1 to 18 carbon atoms, alkyl of 3 to 18 carbon atoms interrupted by —COO—, alkyl of 3 to 18 carbon atoms substituted by COOH or COO—, or $R_2$ is —CH$_2$(OCH$_2$CH$_2$)$_n$ OCH$_3$ where n is 1 to 12, or $R_2$ is cycloalkyl of 5 to 12 carbon atoms, aryl of 6 to 12 carbon atoms, or said aryl substituted by one to four alkyl groups of 1 to 4 carbon atoms, or $R_2$ is —NHR$_3$ where R$_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —N(R$_3$)$_2$ where R$_3$ is as defined above, when m is 2, $R_2$ is alkylene of 1 to 12 carbon atoms, alkenylene of 4 to 12 carbon atoms, xylylene, alkylene of 2 to 12 carbon atoms interrupted by —COO—, alkylene of 3 to 18 carbon atoms substituted by COOH or COO—, or $R_2$ is —CH$_2$(OCH$_2$CH$_2$)$_n$ OCH$_2$— where n is 1 to 12, or $R_2$ is cycloalkylene of 5 to 12 carbon atoms, aralkylene of 7 to 15 carbon atoms or arylene of 6 to 12 carbon atoms, or $R_2$ is —NHR$_4$NH— where R$_4$ is alkylene of 2 to 18 carbon atoms, cycloalkylene of 5 to 12 carbon atoms, aralkylene of 8 to 15 carbon atoms or arylene of 6 to 12 carbon atoms, or $R_2$ is —N(R$_3$)R$_4$N(R$_3$)— where R$_3$ and R$_4$ are as defined above, or $R_2$ is —CO—, —NH—CO—NH—, or —N(R3)-CO—N(R3)-, when m is 3, $R_2$ is alkanetriyl of 3 to 8 carbon atoms or benzenetriyl, or when m is 4, $R_2$ is alkanetetrayl of 5 to 8 carbon atoms or benzenetetrayl, in formula (C*), $R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, x is 1 or 2, and when x is 1, $R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1 st, 2nd or 3rd group of the periodic table or is Zn, Cu, Ni or Co, or M is a group N$^{n+}$(R$_2$)$_4$ where R$_2$ is hydrogen, alkyl of 1 to 8 carbon atoms or benzyl, or when x is 2, $R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula (D*), y is 1 to 4, $R_{10}$ is as defined above, and $R_{12}$ is defined as $R_2$ above, in formula (E*), k is 1 or 2, when k is 1, $R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or $R_{20}$ and $R_{21}$ together are alkylene of 2 to 8 carbon atoms or said alkylene substituted by hydroxyl, or are acyloxy-alkylene of 4 to 22 carbon atoms, or when k is 2, $R_{20}$ and $R_{21}$ are together (—CH$_2$)$_2$C(CH$_2$—)$_2$, in formula (F*), $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, when g is 2, $R_{31}$ is defined as $R_1$ above when n is 2, in formula (G*), $Q_1$ is —NR$_{41}$— or —O—, $E_1$ is alkylene of 1 to 3 carbon atoms, or $E_1$ is —CH$_2$—CH(R$_{42}$)—O— where R$_{42}$ is hydrogen, methyl or phenyl, or $E_1$ is —(CH$_2$)$_3$—NH— or $E_1$ is a direct bond, $R_{40}$ is hydrogen or alkyl of 1 to 18 carbon atoms, $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —CH$_2$—CH(R$_{42}$)—OH where R$_{42}$ is as defined above, in formula (H*), p is 1 or 2, $T_4$ is as defined for R$_{11}$ when x is 1 or 2, M and Y are independently methylene or carbonyl, preferably M is methylene and Y is carbonyl, in formula (I*), this formula denotes a recurring structural unit of a polymer where $T_1$ is ethylene or 1,2-propylene or is the repeating structural unit derived from an alpha-olefin copolymer with an alkyl acrylate or methacrylate, and where q is 2 to 100, $Q_1$ is —N(R$_{41}$)— or —O— where R$_{41}$ is as defined above, in formula (J*), r is 1 or 2, $T_7$ is as defined for $R_1$ when n is 1 or 2 in formula (A*), preferably $T_7$ is octamethylene when r is 2, in formula (L*), u is 1 or 2, $T_{13}$ is as defined for $R_1$ when n is 1 or 2 in formula (A*), with the proviso that $T_{13}$ is not hydrogen when u is 1, in formula (M*), $E_1$ and $E_2$, being different, each are —CO— or —N(E$_5$)— where $E_5$ is hydrogen, alkyl of 1 to 12 carbon atoms or alkoxycarbonylalkyl of 4 to 22 carbon atoms, preferably $E_1$ is —CO— and $E_2$ is —N(E$_5$)—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, preferably methyl, in formula (O*), $R_{10}$ is as defined for $R_{10}$ in formula (C*), in formula (P*), $E_6$ is an aliphatic or aromatic tetravalent radical, preferably neopentanetetrayl or benzenetetrayl, in formula (T*), $R_{51}$ is hydrogen, alkyl of 1 to 18 carbon atoms, cycloalkyl of 5 to 12 carbon atoms, or aryl of 6 to 10 carbon atoms, $R_{52}$ is hydrogen or alkyl of 1 to 18 carbon atoms, or $R_{51}$ and $R_{52}$ together of alkylene of 4 to 8 carbon atoms, f is 1 or 2, when f is 1, $R_{50}$ is as defined for $R_{11}$ in formula (C*) when x is 1, or $R_{50}$ is —$(CH_2)_z COOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl, when f is 2, $R_{50}$ is as defined for $R_{11}$ in formula (C*) when x is 2, in formula (U*), $R_{53}$, $R_{54}$, $R_{55}$ and $R_{56}$ are independently alkyl of 1 to 4 carbon atoms or are together pentamethylene, in formula (V*), $R_{57}$, $R_{58}$, $R_{59}$ and $R_{60}$ are independently alkyl of 1 to 4 carbon atoms or are together pentamethylene, in formula (W*), $R_{61}$, $R_{62}$, $R_{63}$ and $R_{64}$ are independently alkyl of 1 to 4 carbon atoms or are together pentamethylene, $R_{65}$ is alkyl of 1 to 5 carbon atoms, M is hydrogen or oxygen, wherein in formulas (Y*) to (BB*), n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_k O[(CH_2)_k O]_h(CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, in formula (DD*), m is 2 or 3, when m is 2, G is —$(CH_2CHR—O)_rCH_2CHR$—, where r is 0 to 3, and R is hydrogen or methyl, and when m is 3, G is glyceryl, in formula (EE*), $G_2$ is —CN, —$CONH_2$ or —$COOG_3$ where $G_3$ is hydrogen, alkyl of 1 to 18 carbon atoms or phenyl, in formulae (III) to (IIIc)

A11 is $OR_{101}$ or $NR_{111}R_{112}$, $R_{101}$ is alkenyl of 2 to 4 carbon atoms, propargyl, glycidyl, alkyl of 2 to 6 carbon atoms interrupted by one or two oxygen atoms, substituted by one to three hydroxyl groups or both interrupted by said oxygen atoms and substituted by said hydroxyl groups, or $R_{101}$ is alkyl of 1 to 4 carbon atoms substituted by carboxy or by the alkali metal, ammonium or $C_1$-$C_4$alkylammonium salts thereof; or $R_{101}$ is alkyl substituted by $COOE_{10}$ where $E_{10}$ is methyl or ethyl, $R_{102}$ is alkyl of 3 to 5 carbon atoms interrupted by —COO— or by —CO—, or $R_{102}$ is —$CH_2(OCH_2CH_2)_c COCH_3$ where c is 1 to 4; or $R_{102}$ is —$NHR_{103}$ where $R_{103}$ is alkyl of 1 to 4 carbon atoms, a is 2 to 4, when a is 2, $T_{11}$ is —$(CH_2CHR_{100}—O)_d CH_2CHR_{100}$—, where d is 0 or 1, and $R_{100}$ is hydrogen or methyl, when a is 3, $T_{11}$ is glyceryl, when a is 4, $T_{11}$ is neopentanetetrayl, b is 2 or 3, when b is 2, $G_{11}$ is —$(CH_2CHR_{100}—O)_d CH_2CHR_{100}$—, where d is 0 or 1, and $R_{100}$ is hydrogen or methyl, and when b is 3, $G_{11}$ is glyceryl;

$R_{111}$ is hydrogen, unsubstituted alkyl of 1 to 4 carbon atoms, alkyl of 1 to 4 carbon atoms substituted by one or two hydroxyl, alkyl of 1 to 4 carbon atoms interrupted by one or two oxygen atoms, or both substituted by one hydroxyl and interrupted by one or two oxygen atoms, $R_{112}$ is —CO—$R_{113}$ where $R_{113}$ has the same meaning as $R_{111}$, or $R_{113}$ is $NHR_{114}$, wherein $R_{114}$ is unsubstituted alkyl of 1 to 4 carbon atoms, alkyl of 1 to 4 carbon atoms substituted by one or two hydroxyl, alkyl of 1 to 4 carbon atoms substituted by alkoxy of 1 to 2 carbon atoms, or both substituted by one hydroxyl and by alkoxy of 1 to 2 carbon atoms, or $R_{111}$ and $R_{112}$ together are —CO—$CH_2CH_2$—CO—, or $(CH_2)_6 CO$—;

BM is a basic material selected from the group consisting of alkali metal hydroxides, alkaline earth metal hydroxides, and amines;

amines are $R_{115}$—$N(R_{116})$—$R_{117}$, wherein $R_{115}$, $R_{116}$, and $R_{117}$ are independently hydrogen, straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{118}$, —$OR_{119}$, or —$NH_2$ groups or mixtures thereof; or said alkyl or said alkenyl interrupted by one or more —O—, —NH— or —$NR_{119}$— groups or mixtures thereof and which can be unsubstituted or substituted by one or more —OH, —$OR_{119}$ or —$NH_2$ groups or mixtures thereof;

$R_{118}$ is hydrogen, straight or branched chain $C_1$-$C_{18}$alkyl, $C_5$-$C_{12}$cycloalkyl, straight or branched chain $C_3$-$C_8$alkenyl, $C_6$-$C_{14}$aryl or $C_7$-$C_{15}$aralkyl, $R_{119}$ is straight or branched chain alkyl of 1 to 18 carbon atoms;

alkali metal hydroxide is sodium hydroxide, potassium hydroxide, or rubidium hydroxide;

alkaline earth metal hydroxide is magnesium hydroxide, calcium hydroxide, strontium hydroxide, or barium hydroxide;

HY is an inorganic or organic acid; wherein the total charge of cations is equal to the total charge of anions; and Y is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, a carboxylate of hydroxyethylethylenediaminetriacetic acid, a carboxylate of ethylenediamine-tetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

Another embodiment of the instant invention is the compounds of component (b) formula (I) selected from the group consisting of (A*), (B*), (C*), (D*), (Q*), (R*), (Y*), and (Z*), wherein E is alkoxy of 1 to 10 carbon atoms, cycloalkoxy of 5 to 8 carbon atoms or aralkoxy of 7 to 12 carbon atoms, or E is —O-T-(OH)$_b$, T is a straight or branched chain alkylene of 1 to 10 carbon atoms, cycloalkylene of 5 to 10 carbon atoms, cycloalkenylene of 5 to 10 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen;

in formula (A*), n is 1 or 2, when n is 1, $R_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen or alkyl of 1 to 4 carbon atoms, when n is 2, $R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups, in formula (B*), m is 1 or 2 when m is 1, $R_2$ is alkyl of 1 to 4 carbon atoms or $R_2$ is $CH_2(OCH_2CH_2)_n OCH_3$ where n is 1 to 12, or $R_2$ is phenyl, or said phenyl substituted by one to three methyl groups, or $R_2$ is —$NHR_3$ where $R_3$ is alkyl of 1 to 4 carbon atoms or phenyl, or said phenyl substituted by one or two methyl groups, when m is 2, $R_2$ is alkylene of 1 to 8 carbon atoms, alkenylene of 4 to 8 carbon atoms, or $R_2$ is —$CH_2(OCH_2CH_2)_nOCH_2$— where n is 1 to 12, or $R_2$ is —$NHR_4NH$— where $R_4$ is of 2 to 6 carbon atoms, aralkylene of 8 to 15 carbon atoms or arylene of 6 to 12 carbon atoms, or $R_2$ is —CO— or —NHCONH—, in formula (C*), $R_{10}$ is hydrogen or, alkanoyl of 1 to 3 carbon atoms, x is 1 or 2, when x is 1, $R_{11}$ is hydrogen, alkyl of 1 to 6 carbon atoms or glycidyl, or $R_{11}$ is alkyl of 1 to 4 carbon atoms substituted by a carboxy group or by COOZ where Z is hydrogen or alkyl of 1 to 4 carbon atoms, when x is 2, $R_{11}$ is alkylene of 1 to 6 carbon atoms, in formula (D*), $R_{10}$ is hydrogen, y is 1 or 2, $R_{12}$ is defined as $R_2$ above, in formula (Y*) and (Z*), x is 1 or 2, when x is 1, $R_1$ and $R_2$ are independently alkyl of 1 to 4 carbon atoms or $R_1$ and $R_2$ are together tetramethylene, or pentamethylene, $R_2$ is hydrogen or alkyl of 1 to 4 carbon atoms, said alkyl group substituted by a hydroxyl group, when x is 2, $R_1$ is hydrogen, alkyl of 1 to 4 carbon atoms, said alkyl substituted by a hydroxyl group, $R_2$ is alkylene of 2 to 6 carbon atoms, $R_3$ is as defined above, BM is a basic material selected from the group consisting of alkali metal hydroxides, alkaline earth metal hydroxides, and amines;

amines are $R_{115}$—N($R_{116}$)—$R_{117}$, wherein $R_{115}$, $R_{116}$, and $R_{117}$ are independently hydrogen, straight or branched alkyl chain of 1 to 18 carbon atoms, straight or branched chain alkenyl of 2 to 12 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —$OR_{119}$, or —$NH_2$ groups or mixtures thereof; or said alkyl or said alkenyl interrupted by one or more —O—, —NH— or —$NR_{119}$— groups or mixtures thereof and which can be unsubstituted or substituted by one or more —OH, —$OR_{119}$ or —$NH_2$ groups or mixtures thereof;

$R_{119}$ is straight or branched chain alkyl of 1 to 12 carbon atoms;

alkali metal hydroxide is sodium hydroxide or potassium hydroxide;

alkaline earth metal hydroxide is magnesium hydroxide or calcium hydroxide;

HY is an inorganic or organic acid; and, wherein the total charge of cations is equal to the total charge of anions; and Y is phosphate, phosphonate, carbonate, bicarbonate, chloride, bromide, bisulfate, sulfate, borate, formate, acetate, benzoate, citrate, oxalate, tartrate, acrylate, fumarate, maleate, itaconate, glycolate, gluconate, malate, mandelate, tiglate, ascorbate, a carboxylate of nitrilo-triacetic acid, a carboxylate of hydroxyethylethylenediaminetriacetic acid, a carboxylate of ethylenediaminetetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

Still another embodiment of the instant invention is the compounds of component (b) formula (I) selected from the group consisting of (A*), (B*), (C*), (D*), (Q*), and (R*),
wherein
E is alkoxy of 1 to 10 carbon atoms, cycloalkoxy of 5 to 8 carbon atoms or aralkoxy of 7 to 12 carbon atoms, or E is —O-T-(OH)$_b$, T is a straight or branched chain alkylene of 1 to 10 carbon atoms, cycloalkylene of 5 to 10 carbon atoms, cycloalkenylene of 5 to 10 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen,
in formula (A*),
h is 1,
$R_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or $R_1$ is alkyl of 1 to 4 carbon atoms substituted by —COOZ where Z is hydrogen or alkyl of 1 to 4 carbon atoms,
in formula (B*),
m is 1 or 2,
$R_2$ is alkyl of 1 to 4 carbon atoms or $R_2$ is $CH_2(OCH_2CH_2)_n OCH_3$ where n is 1 to 4,
when m is 2,
$R_2$ is alkylene of 1 to 8 carbon atoms,
in formula (C*),
$R_{10}$ is hydrogen or alkanoyl of 1 or 2 carbon atoms,
x is 1 or 2,
when x is 1,
$R_{11}$ is hydrogen, alkyl of 1 to 4 carbon atoms or glycidyl,
$R_{11}$ is alkyl of 1 to 4 carbon atoms substituted by COOZ where Z is hydrogen or alkyl of 1 to 4 carbon atoms,
when x is 2,
$R_{11}$ is alkylene of 1 to 6 carbon atoms,
in formula (D*),
$R_{10}$ is hydrogen,
y is 1 or 2,
$R_{12}$ is defined as $R_2$ above;
when x is 1,
$R_{11}$ is hydrogen, alkyl of 1 to 6 carbon atoms or glycidyl, or
$R_{11}$ is alkyl of 1 to 4 carbon atoms substituted by a carboxy group or by COOZ where Z is hydrogen or alkyl of 1 to 4 carbon atoms,
when x is 2,
$R_{11}$ is alkylene of 1 to 6 carbon atoms,
in formula (D*),
$R_{10}$ is hydrogen,
y is 1 or 2,
$R_{12}$ is defined as $R_2$ above, in formula (Y*) and (Z*),
x is 1 or 2,
when x is 1,
$R_1$ and $R_2$ are independently alkyl of 1 to 4 carbon atoms or $R_1$ and $R_2$ are together tetramethylene, or pentamethylene,
$R_2$ is hydrogen or alkyl of 1 to 4 carbon atoms, said alkyl group substituted by a hydroxyl group,
when x is 2,
$R_1$ is hydrogen, alkyl of 1 to 4 carbon atoms, said alkyl substituted by a hydroxyl group,
$R_2$ is alkylene of 2 to 6 carbon atoms,
$R_3$ is as defined above,
BM is a basic material selected from the group consisting of alkali metal hydroxides, alkaline earth metal hydroxides, and amines;
amines are $R_{115}$—N($R_{116}$)—$R_{117}$, wherein
$R_{115}$, $R_{116}$, and $R_{117}$ are independently hydrogen, straight or branched alkyl chain of 1 to 12 carbon atoms, or said alkyl substituted by one or more —OH, —$OR_{119}$, or —$NH_2$ groups or mixtures thereof; or said alkyl interrupted by one or more —O—, —NH— or —$NR_{119}$— groups or mixtures thereof and which can be unsubstituted or substituted by one or more —OH, —$OR_{119}$ or —$NH_2$ groups or mixtures thereof;
$R_{119}$ is straight or branched chain alkyl of 1 to 8 carbon atoms;
Alkali metal hydroxide is sodium hydroxide or potassium hydroxide;
Alkaline earth metal hydroxide is calcium hydroxide;
HY is an inorganic or organic acid; and, wherein the total charge of cations is equal to the total charge of anions; and Y is phosphate, phosphonate, carbonate, bicarbonate, chloride, bromide, bisulfate, sulfate, borate, formate, acetate, benzoate, citrate, oxalate, tartrate, ascorbate, acrylate, fumarate, maleate, itaconate, glycolate, gluconate, malate, mandelate, tiglate, a carboxylate of nitrilo-triacetic acid, a carboxylate of hydroxyethylethylenediaminetriacetic acid, a carboxylate of ethylenediaminetetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

Yet another embodiment of the instant invention is a compound of component (b) formula (I) selected from the group consisting of
(a) Monosodium 1-methoxy-2,2,6,6-tetramethyl-4-acetoxypiperidinium citrate;
(b) Monopotassium 1-methoxy-2,2,6,6-tetramethyl-4-acetamidopiperidinium phosphate;
(c) Monoammonium 1-butoxy-2,2,6,6-tetramethyl-4-acetamidopiperidinium sulfate;
(d) Mono-(N,N,N-triethylammonium) 1-phenoxy-2,2,6,6-tetramethyl-4-methoxy-piperidinium tartrate;
(e) Mono-[N,N-di-n-butyl ammonium]1-ethoxy-2,2,6,6-tetramethyl-4-acetoxypiperidinium maleate;
(f) Mono-[N,N,N-(2-hydroxyethyl)ammonium]1-methoxy-2,2,6,6-tetramethyl-4-propoxy-piperidinium oxalate;
(g) Monosodium 1-methoxy-2,2,6,6-tetramethyl-4-(2-hydroxy-4-oxapentoxy)piperidinium carbonate;
(h) Dipotassium 1-(2-hydroxy-2-methylpropoxy)-2,2,6,6-tetramethyl-4-hydroxypiperidinium citrate;
(i) Monosodium bis(1-(2-hydroxy-2-methylpropoxy)-2,2,6,6-tetramethyl-4-hydroxypiperidinium)citrate;
(j) Diammonium (1-(2-hydroxy-2-methylpropoxy)-2,2,6,6-tetramethyl-4-hydroxypiperidinium)citrate;
(k) Monopotassium monosodium bis(1-(2-hydroxy-2-methylpropoxy)-2,2,6,6-tetramethyl-4-hydroxypiperidinium) ethylenediaminetetraacetate;

(l) Monosodium tris(1-(2-hydroxy-2-methylpropoxy)-2,2,6,6-tetramethyl-4-acetamidopiperidinium)ethylenediaminetetraacetate;

(m) Monocalcium bis(1-(2-hydroxy-2-methylpropoxy)-2,2,6,6-tetramethyl-4-oxopiperidinium)ethylenediaminetetraacetate;

(n) Monoammonium tetra(1-(2-hydroxy-2-methylpropoxy)-2,2,6,6-tetramethyl-4-hydroxypiperidinium)diethylenetriaminepentaacetate;

(o) Disodium tris(1-(2-hydroxy-2-methylpropoxy)-2,2,6,6-tetramethyl-4-acetamidopiperidinium)diethylenetriaminepentaacetate;

(p) Tripotassium di(1-(2-hydroxy-2-methylpropoxy)-2,2,6,6-tetramethyl-4-oxopiperidinium)diethylenetriaminepentaacetate;

(q) Monobenzylammonium bis(1-(2-hydroxy-2-methylpropoxy)-2,2,6,6-tetramethyl-4-hydroxypiperidinium)nitrilotriacetate;

(r) Di-[N,N-diethylammonium]mono(1-(2-hydroxy-2-methylpropoxy)-2,2,6,6-tetramethyl-4-acetamidopiperidinium)nitrilotriacetate;

(s) Monosodium bis(1-(2-hydroxy-2-methylpropoxy)-2,2,6,6-tetramethyl-4-oxopiperidinium)nitrilotriacetate;

(t) Diammonium tris(1-(2-hydroxy-2-methylpropoxy)-2,2,6,6-tetramethyl-4-hydroxypiperidinium)diethylenetriaminepentamethylenephosphonate;

(u) Monosodium tetra(1-(2-hydroxy-2-methylpropoxy)-2,2,6,6-tetramethyl-4-acetamidopiperidinium)diethylenetriaminepentamethylenephosphonate; and, (v) Tripotassium bis(1-(2-hydroxy-2-methylpropoxy)-2,2,6,6-tetramethyl-4-oxopiperidinium)diethylenetriaminepentamethylenephosphonate.

The compounds of component (b) formula (I) can be prepared according to methods known in the art or in analogy to those methods. For example, these compounds may be prepared according to U.S. Pat. No. 6,392,041; U.S. Pat. No. 6,586,507; U.S. Pat. No. 6,166,212; U.S. Pat. No. 5,374,729; U.S. Pat. No. 5,015,683; U.S. Pat. No. 5,021,483; U.S. Pat. No. 4,921,962; U.S. Pat. No. 5,112,890; and, U.S. Pat. No. 5,204,473, incorporated herein by reference.

The present compositions may comprise further traditional additives, for example ultraviolet (UV) light absorbers and antioxidants.

The present invention pertains to a stabilized composition comprising (a) a body care product, household product, textile or fabric, (b) an effective stabilizing amount of one or more compounds of formula (I), and (c) one or more compounds selected from the group consisting of the ultraviolet light absorbers, antioxidants, tocopherol, tocopherol acetate, hindered amine light stabilizers, complex formers, optical brighteners, surfactants, and polyorganosiloxanes.

The additional additives of present component (c) are for example those disclosed in co-pending U.S. application Ser. Nos. 09/830,788, filed May 1, 2001 and 09/830,787, filed May 1, 2001, published as WO 00/25730 and WO 00/25731. The disclosures of these co-pending applications are hereby incorporated by reference.

The UV absorbers are for example selected from group consisting of the 2H-benzotriazoles, the s-triazines, the benzophenones, the alpha-cyanoacrylates, the oxanilides, the benzoxazinones, the benzoates and the alpha-alkyl cinnamates.

The UV absorbers are for example
2,4,6-tris(2-hydroxy-4-octyloxyphenyl)-1,3,5-triazine;
2-(2,4-dihydroxyphenyl)-4,6-bis(2,4-dimethylphenyl)-1,3,5-triazine;
2,4-bis(2-hydroxy-4-propyloxyphenyl)-6-(2,4-dimethylphenyl)-1,3,5-triazine;
2-(2-hydroxy-4-octyloxyphenyl)-4,6-bis(4-methylphenyl)-1,3,5-triazine;
2-(2-hydroxy-4-dodecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine;
2-[2-hydroxy-4-(2-hydroxy-3-octyloxypropyloxy)phenyl]-4,6-bis(2,4-dimethylphenyl)-1,3,5-triazine;
2-[2-hydroxy-4-(2-hydroxy-3-tridecyloxy-propyloxy)phenyl]-4,6-bis(2,4-dimethylphenyl)-1,3,5-triazine;
5-chloro-2-(2-hydroxy-3,5-di-tert-butylphenyl)-2H-benzotriazole;
2-(2-hydroxy-3-dodecyl-5-methylphenyl)-2H-benzotriazole;
5-chloro-2-(2-hydroxy-3-tert-butyl-5-methylphenyl)-2H-benzotriazole;
bis-(3-(2H-benzotriazol-2-yl)-2-hydroxy-5-tert-octyl)methane;
2-(2-hydroxy-3,5-di-tert-butylphenyl)-2H-benzotriazole;
2-(2-hydroxy-3,5-di-tert-amylphenyl)-2H-benzotriazole;
2-(2-hydroxy-3,5-di-alpha?cumylphenyl)-2H-benzotriazole;
2-(2-hydroxy-3-alpha-cumyl-5-tert-octylphenyl)-2H-benzotriazole;
2-(2-hydroxy-5-tert-octylphenyl)-2H-benzotriazole;
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
12-hydroxy-3,6,9-trioxadodecyl 3-tert-butyl-4-hydroxy-5-(2H-benzotriazol-2-yl)-hydro-cinnamate;
octyl 3-tert-butyl-4-hydroxy-5-(2H-benzotriazol-2-yl)-hydrocinnamate;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
4,6-bis(2,4-dimethylphenyl)-2-(4-octyloxy-2-hydroxyphenyl)-s-triazine;
2,4-dihydroxybenzophenone;
2,2'-dihydroxy-4,4'-dimethoxy-5,5'-disulfobenzophenone, disodium salt;
2-hydroxy-4-octyloxybenzophenone;
2-hydroxy-4-dodecyloxybenzophenone;
2,4-dihydroxybenzophenone;
2,2',4,4'-tetrahydroxybenzophenone;
4-aminobenzoic acid;
2,3-dihydroxypropyl-4-aminobenzoic acid;
3-(4-imidazolyl)acrylic acid;
2-phenyl-5-benzimidazole sulfonic acid;
N,N,N-trimethyl-alpha-(2-oxo-3-bornylidene)-p-toluidinium methyl sulfate;
5-benzoyl-4-hydroxy-2-methoxybenzenesulfonic acid, sodium salt;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
2-(2-hydroxy-5-methylphenyl)-2H-benzotriazole; or
2,2'-dihydroxy-4,4'-dimethoxybenzophenone (Uvinul® 3049).

For instance, suitable UV absorbers are selected from
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
2-(2-hydroxy-3,5-di-tert-butylphenyl)-2H-benzotriazole;
2-(2-hydroxy-3,5-di-tert-amylphenyl)-2H-benzotriazole;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
12-hydroxy-3,6,9-trioxadodecyl 3-tert-butyl-4-hydroxy-5-(2H-benzotriazol-2-yl)-hydro-cinnamate;
2,4-dihydroxybenzophenone;
2,2'-dihydroxy-4,4'-dimethoxy-5,5'-disulfobenzophenone, disodium salt;
2,2',4,4'-tetrahydroxybenzophenone;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
5-benzoyl-4-hydroxy-2-methoxy-benzenesulfonic acid, sodium salt; or
2-(2-hydroxy-3-alpha-cumyl-5-tert-octylphenyl)-2H-benzotriazole.

Additional suitable antioxidants are for example selected from the hindered phenolic and benzofuranone stabilizers.

Suitable antioxidants are for example selected from the group consisting of

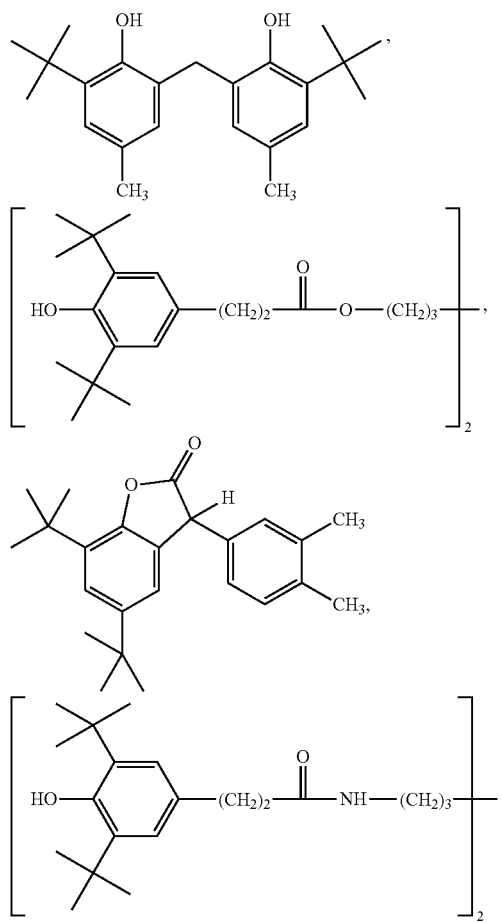

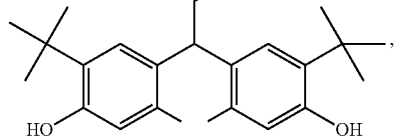

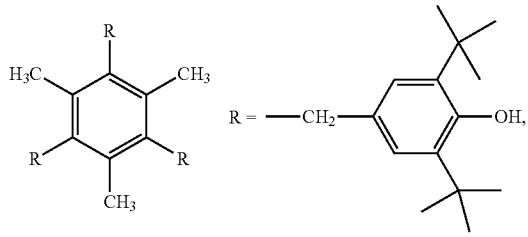

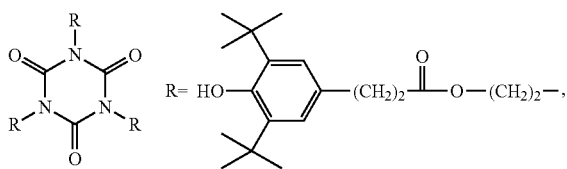

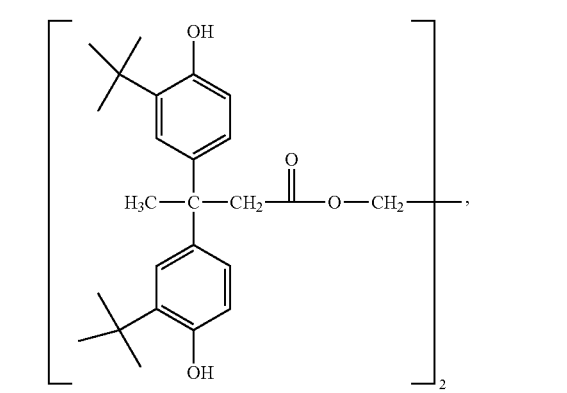

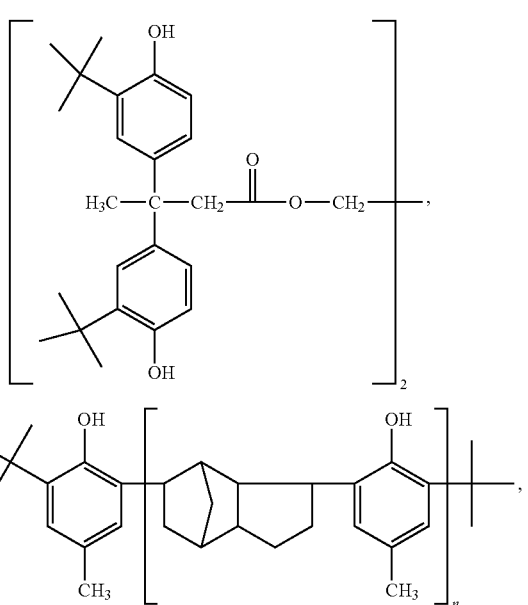

$n = 1-3$

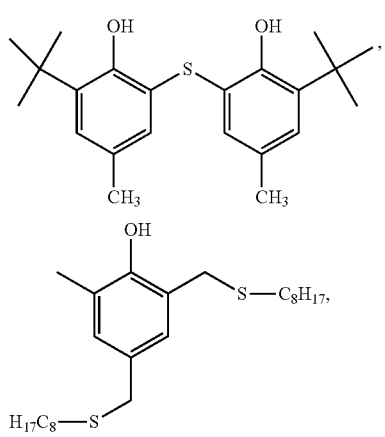

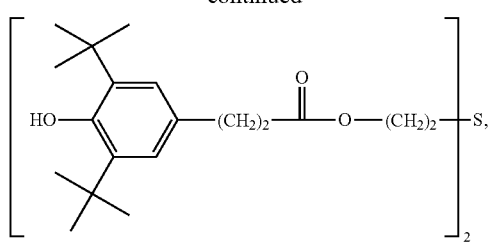
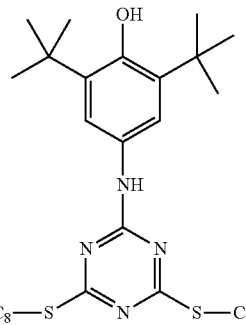
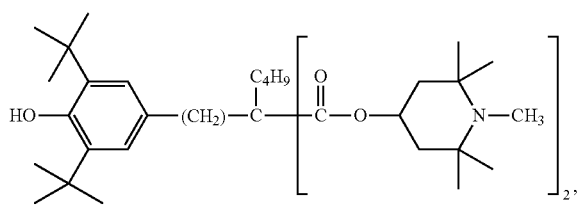
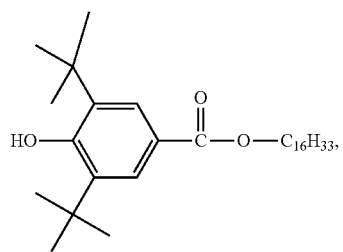
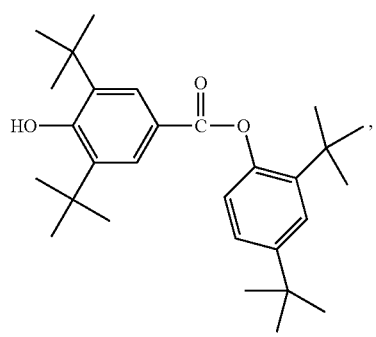
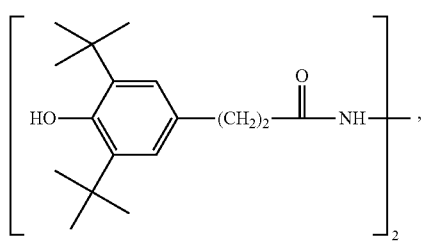
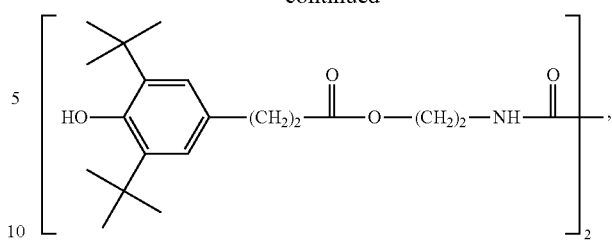
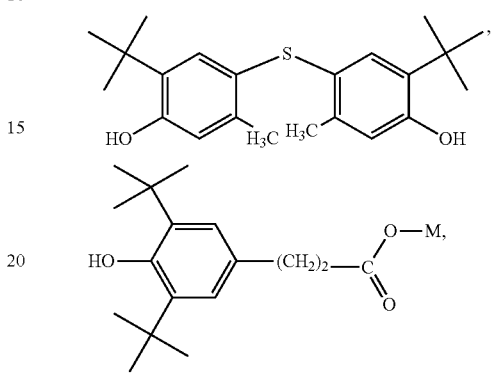
M = H, ammonium, alkali
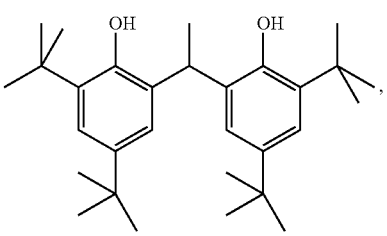
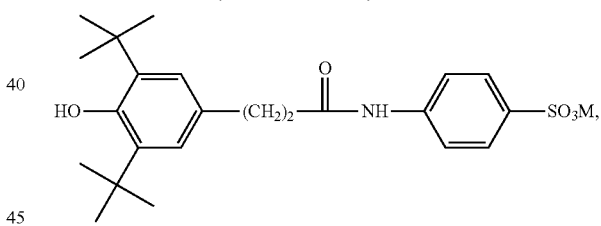
M = H, Na
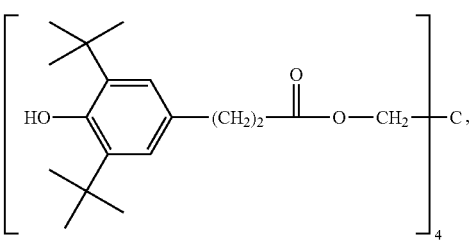
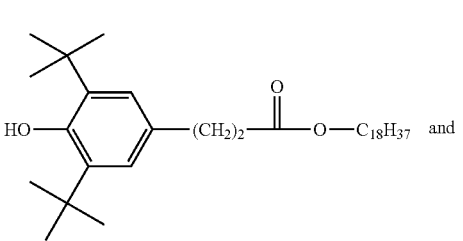
and

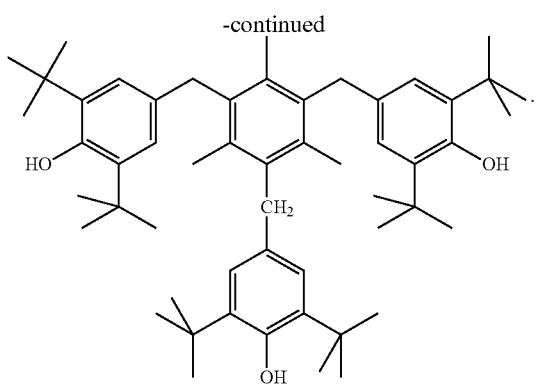

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxy-benzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro-[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-di-aza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

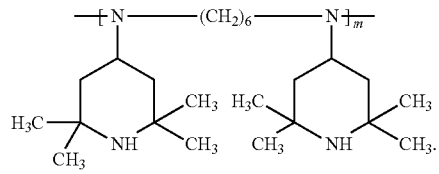

wherein m is a value from 5-50,

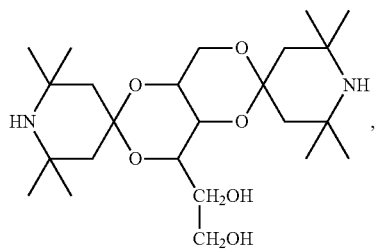

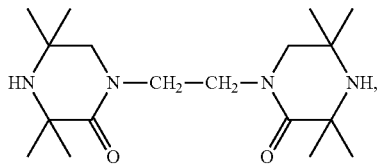

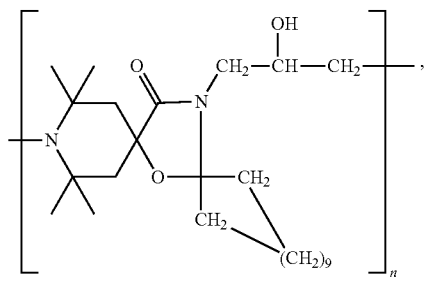

-continued

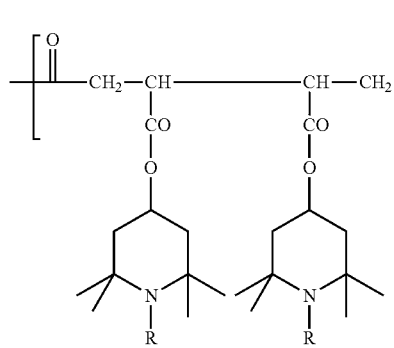
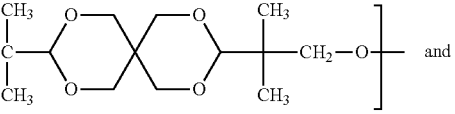

where R = H or CH₃

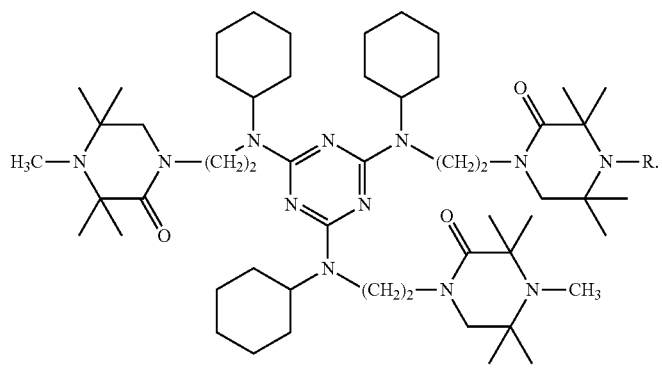

where R = H or CH₃

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers are for example selected from the group consisting of ethylenediaminetetracetic acid (EDTA), nitrilotriacetic acid (NTA), beta-alaninediacetic acid (EDETA) or ethylenediaminedisuccinic acid (EDDS),

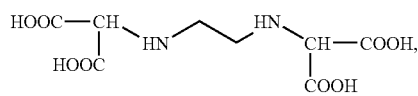

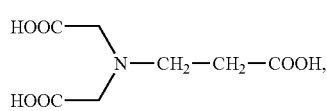

aminetrimethylenephosphoric acid (ATMP) conforming to formula

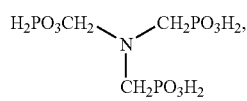

serinediacetic acid (SDA) conforming to formula

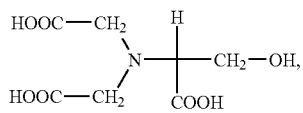

asparaginediacetic acid conforming to formula

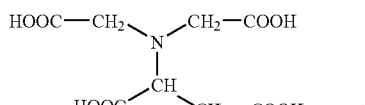
and methylglycinediacetic acid (MGDA) conforming to formula

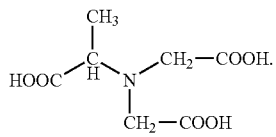

The present stabilizer systems are particularly suitable for stabilizing body care products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present body care products can be in the form of creams, ointments, pastes, foams, gels, lotions, powders, make-ups, sprays, sticks or aerosols. The present stabilizer systems may be present in the oil phase or in the aqueous or aqueous/alcoholic phase.

The additives of component (b) are present, for example, in the body care and household products in a concentration of about 5 to about 10000 ppm, based on the total formulation by weight, for example from about 10 to about 5000 ppm, for example from about 100 to about 5000 ppm. For example the additives of component (b) are present in the body care and household products in a concentration of about 5, 10, 15, 20, 25, 35, 40, 45 or 50 ppm, based on the total formulation by weight. For example, the additives of component (b) are present from about 5 to about 5000 ppm in the formulations (compositions) of this invention.

Laundry detergents, fabric softeners or other products, from which the additives of component (b) are intended for deposition onto fabrics with use, are considered household products of this invention, and the above concentration levels also pertain thereto. The present additives of component (b) are effective at stabilizing the laundry detergents and fabric softeners, as well as the fabrics treated therewith.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropyl-myristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturisers and wetting agents, such as polyoxyethylenesobitan fatty acid ester. The gels furthermore contain commercially available preservatives, such as benzyl alcohol, phenethyl alcohol, phenoxyethanol and the like.

The following is a list of examples of body care products of this invention and their ingredients:

| Body care product | Ingredients |
| --- | --- |
| moisturising cream | vegetable oil, emulsifier, thickener, perfume, water, antioxidant, UV absorbers |
| shampoo | surfactant, emulsifier, preservatives, perfume, antioxidant, UV absorbers |
| toothpaste | cleaning agent, thickener, sweetener, flavor, colorant, antioxidant, water, UV absorbers |
| lip-care stick | vegetable oil, wax, $TiO_2$, antioxidant, UV absorbers |

The present body care products, household products, textiles and fabrics have high stability towards color changes and chemical degradation of the ingredients present in these products. For example, present compositions that comprise a dye are found to have excellent color stability.

Accordingly, the present invention further pertains to a stabilized composition comprising (a) a body care product, household product, textile or fabric, (b) an effective stabilizing amount of one or more compounds of formula (I), and (d) a dye.

Dyes according to the present invention are for example:

inorganic pigments, for example iron oxide (Iron Oxide Red, Iron Oxide Yellow, Iron Oxide Black, etc.), Ultramarines, Chromium Oxide Green or Carbon Black;

natural or synthetic organic pigments;

disperse dyes which may be solubilzed in solvents like direct hair dyes of the HC type, for example HC Red No. 3, HC Blue No. 2 and all other hair dyes listed in International Cosmetic Ingredient Dictionary and Handbook, 7$^{th}$ edition 19997) or the dispersion dyes listed in Color Index International or Society of Dyers and Colourists;

color varnishes (insoluble salts of soluble dyes, like many Ca-, Ba- or Al-salts of anionic dyes);

soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wavelength of ca. 4000 to 700 nm). The absorption is often caused by the following chromophores:

Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present stabilizer systems are also used in household cleaning and treatment agents, for example in laundry products and fabric softeners, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and solid and liquid air fresheners.

The present invention also concerns home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

The stabilizers of the present invention may be employed in fabric treatment that takes place after use of the fabric, referred to as fabric care. Such treatments include laundering, which uses detergents and/or fabric conditioner, and the application of non-detergent based fabric care products, such as spray-on products. When employed in this fashion, the present stabilizers are intended for deposition onto the fabric and used to protect the fabric, colorants and fragrances associated with said these fabrics from environmental damage.

Typical examples of household cleaning and treating agents are:

| Household cleaners/household treating agents | Ingredients |
| --- | --- |
| detergent concentrate | surfactant mixture, ethanol, antioxidant, water, UV absorbers, antioxidant |
| shoe polish | wax, wax emulsifier, antioxidant, water, preservative, UV absorbers, antioxidant |
| wax-containing floor cleaning agent | emulsifier, wax, sodium chloride, antioxidant, water, preservative, UV absorbers, antioxidant |

The present stabilizers are for example incorporated by dissolution in an oil phase or alcoholic or water phase, where required at elevated temperature.

The present invention also pertains to a method of stabilizing a body care product, household product, textile or fabric, which comprises incorporating therein or applying thereto one or more compounds of the formulae (III) to (IIIc), for example one or more compounds of the formulae A* to EE*.

In the case of stabilized fabrics, for example dyed fabrics, the present stabilizers are applied thereto via deposition from for instance detergents, fabric conditioners or non-detergent based fabric care products.

The present fabrics are natural or synthetic, and may be woven or nonwoven.

The present invention also pertains to a method of stabilizing a body care product, household product, textile or fabric, each of which contain a dye, which comprises incorporating therein or applying thereto one or more compounds of the formulae (III) to (IIIc), for example one or more compounds of the formulae A* to EE*. The stabilizers of formulae (III) to (IIIc) are very effective towards the stabilization of dyes in the present compositions.

The textiles of this invention are for example textile fiber materials, for example nitrogen-containing or hydroxy-group-containing fiber materials, for instance textile fiber materials selected from cellulose, silk, wool, synthetic polyamides, leather and polyurethanes. Included are cotton, linen and hemp, pulp and regenerated cellulose. Included also are cellulosic blends, for example mixtures of cotton and polyamide or cotton/polyester blends.

The additives of the present invention are for example applied to textiles in a dyeing or printing process, or in a finishing process. For instance, the additives may be applied as part of a dye formulation. The additives may be applied to textiles for example in an ink-jet printing process. The additives are for example applied as part of an aqueous dye solution or printing paste. They may be applied in an exhaust method or dyeing by the padder dyeing method, in which the textiles are impregnated with aqueous dye solutions, which may contain salts, and the dyes and additives are fixed, after an alkali treatment or in the presence of alkali, if appropriate with the action of heat or by storage at room temperature for several hours. After fixing, the dyeings or prints are rinsed thoroughly with cold and hot water, if appropriate with the addition of an agent which has a dispersing action and promotes diffusion of the non-fixed portions.

The dye or ink formulations for application to textiles may comprise further customary additives, for example surfactants, antifoams, antimicrobials and the like, for example as disclosed in U.S. Pat. Nos. 6,281,339, 6,353,094 and 6,323,327, the disclosures of which are hereby incorporated by reference.

The following Examples illustrate the invention. Percentages are in weight percent unless indicated otherwise.

About 20 mL of each of the aqueous test formulations are placed in a borosilicate glass bottle.

The bottles are also exposed to accelerated fluorescent lighting, Philips, 40 Watt, Daylight Deluxe (D65), full exposure to light.

Example 1

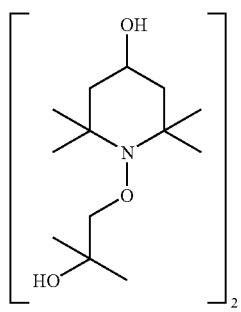

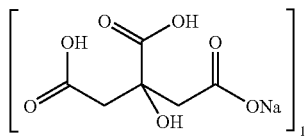

4-Hydroxy-1-(2-hydroxy-2-methylpropoxy)-2,2,6,6-tetramethylpiperidine (5 g, 0.02 mole), citric acid (4.29 g, 0.02 mole), water (50 g, 2.8 mole), sodium hydroxide (0.8 g, 0.02 mole) and methanol (400 g, 12.5 mole) are added to a round bottom flask. The mixture is heated to 50 C and stirred for 60 minutes to ensure complete dissolution. The methanol and water are removed by distillation and the resulting solid product is dried to constant weight. The title compound is obtained (8.3 g, 83% yield) as a white solid with a melting point of 123-131 C whose structure is consistent with HNMR. The HNMR spectrum indicates a ratio of about two to one.

$^1$H NMR (CD$_3$OD): δ 3.88 (t, 1H), 3.63 (s, 2H), 2.80 (s, 4H), 1.75 (d, 2H), 1.42 (t, 2H), 1.23 (s, 6H), 1.21 (s, 6H), 1.20 (s, 6H).

Example 2

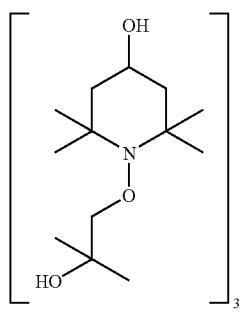

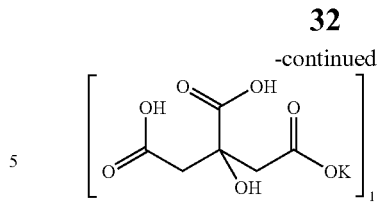

4-Hydroxy-1-(2-hydroxy-2-methylpropoxy)-2,2,6,6-tetramethylpiperidine (5 g, 0.02 mole), citric acid (4.29 g, 0.02 mole), water (50 g, 2.8 mole), potassium hydroxide (1.33 g, 0.02 mole) and methanol (400 g, 12.5 mole) are added to a round bottom flask. The mixture is heated to 50 C and stirred for 60 minutes to ensure complete dissolution. The methanol and water are removed by distillation and the resulting solid product is dried to constant weight. The title compound is obtained (8.4 g, 82% yield) as a white solid with a melting point of 124-132 C whose structure is consistent with HNMR. The HNMR spectrum indicates a ratio of about three to one.

$^1$H NMR (CD$_3$OD): δ 3.88 (t, 1H), 3.63 (s, 2H), 2.79 (q, 4H), 1.75 (d, 2H), 1.42 (t, 2H), 1.23 (s, 6H), 1.21 (s, 6H), 1.20 (s, 6H).

Example 3

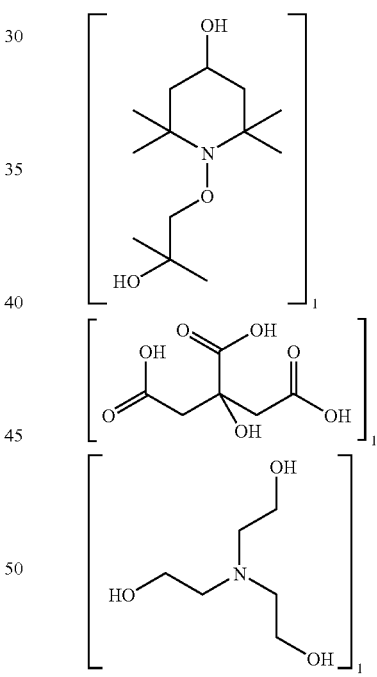

4-Hydroxy-1-(2-hydroxy-2-methylpropoxy)-2,2,6,6-tetramethylpiperidine (5 g, 0.02 mole), citric acid (4.29 g, 0.02 mole), triethanolamine (3.1 g, 0.02 mole), and methanol (100 g, 3.2 mole) are added to a round bottom flask. The mixture is stirred at ambient temperature for 30 minutes to ensure complete dissolution. The methanol is removed by distillation and the resulting solid product is dried to constant weight. The title compound is obtained (9.8 g, 80% yield) as a white, waxy solid with a melting point of 133-136 C whose structure is consistent with HNMR. The HNMR spectrum indicates a ratio of about one to one to one.

$^1$H NMR (CD$_3$OD): δ 3.89 (t, 6H), 3.88 (t, 1H), 3.63 (s, 2H), 3.41 (t, 6H), 2.77 (q, 4H), 1.75 (d, 2H), 1.42 (t, 2H), 1.23 (s, 6H), 1.21 (s, 6H), 1.20 (s, 6H).

Anal. Calcd for C$_{25}$H$_{50}$N$_2$O$_{13}$: C, 51.18; H, 8.59; N, 4.77. Found: C, 51.48; H, 8.76; N, 4.61.

Example 4

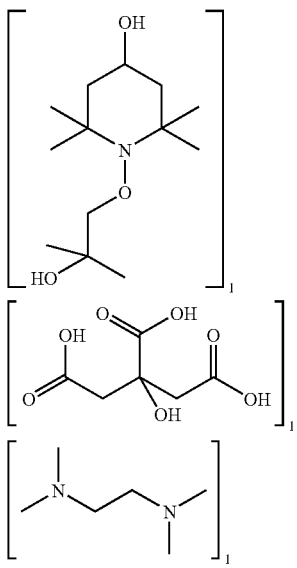

4-Hydroxy-1-(2-hydroxy-2-methylpropoxy)-2,2,6,6-tetramethylpiperidine (5 g, 0.02 mole), citric acid (4.29 g, 0.02 mole), N,N,N',N'-tetramethylethylenediamine (2.37 g, 0.02 mole), and methanol (100 g, 3.2 mole) are added to a round bottom flask. The mixture is stirred at ambient temperature for 30 minutes to ensure complete dissolution. The methanol is removed by distillation and the resulting solid product is dried to constant weight. The title compound is obtained (10.2 g, 88% yield) as a white solid with a melting point of 110-129 C whose structure is consistent with HNMR. The HNMR spectrum indicates a ratio of about one to one to one.

$^1$H NMR (CD$_3$OD): δ 3.88 (t, 1H), 3.63 (s, 2H), 3.05 (s, 4H), 2.75 (q, 4H), 2.65 (s, 12H), 1.75 (d, 2H), 1.42 (t, 2H), 1.23 (s, 6H), 1.21 (s, 6H), 1.20 (s, 6H).

Anal. Calcd for C$_{25}$H$_{51}$N$_3$O$_{10}$: C, 54.23; H, 9.28; N, 7.59. Found: C, 53.61; H, 9.28; N, 7.09.

Example 5

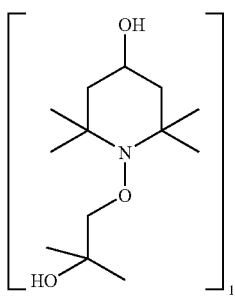

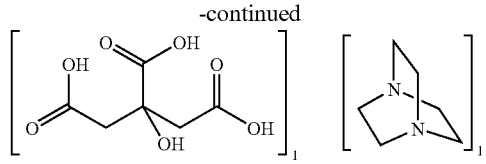

4-Hydroxy-1-(2-hydroxy-2-methylpropoxy)-2,2,6,6-tetramethylpiperidine (5 g, 0.02 mole), citric acid (4.29 g, 0.02 mole), 1,4-diazabicyclo[2.2.2]octane (2.24 g, 0.02 mole), and methanol (200 g, 6.4 mole) are added to a round bottom flask. The mixture is stirred at ambient temperature for 30 minutes to ensure complete dissolution. The methanol is removed by distillation and the resulting solid product is dried to constant weight. The title compound is obtained (9.8 g, 85% yield) as a white, crystalline solid with a melting point of 132-135 C whose structure is consistent with HNMR. The HNMR spectrum indicates a ratio of about one to one to one.

$^1$H NMR (CD$_3$OD): δ 3.88 (t, 1H), 3.63 (s, 2H), 3.18 (s, 12H), 3.05 (s, 4H), 2.75 (q, 4H), 2.65 (s, 12H), 1.75 (d, 2H), 1.42 (t, 2H), 1.23 (s, 6H), 1.21 (s, 6H), 1.20 (s, 6H).

Example 6

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Suave® Natural Fresh Mountain Strawberry Shampoo) with agitation. The stabilized shampoo formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE). The color change is given by Delta E (DE) which is calculated by:

$$DE=[(DL^*)^2+(Da^*)^2+(Db^*)^2]^{1/2}$$

| Stabilizer (loading at 0.30 wt %) | DE after 4 weeks |
| --- | --- |
| None | 21.6 |
| Example 2 | 20.5 |
| Example 1 | 18.0 |
| Example 3 | 16.8 |
| Example 5 | 15.4 |

The compounds according to this invention are able to improve clearly the light fastness of shampoo formulations.

Example 7

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Clairol® Herbal Essences Shampoo) with agitation. The stabilized shampoo formulation is agitated for 15 minutes and put into 20 mL glass scintillation vials. These formulations are weathered under fluorescent light aging at ambient temperature. The ClEL*a*b coordinates before and after exposure are measured using X-Rite 938 Spectrodensitometer. Color change is expressed as Delta E (DE).

| Stabilizer (loading at 0.30 wt %) | DE after 1 week |
|---|---|
| Compound A | 1.32 |
| Example 2 | 1.16 |

Compound A is 1-oxyl-2,2,6,6-tetramethyl-4-hydroxypiperidine which is disclosed in WO2003103622, the publication of U.S. Pat. app. No. 60/377,381, filed May 2, 2002, incorporated herein by reference.

The compounds according to this invention are able to improve clearly the light fastness of shampoo formulations.

Example 8

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Scope® Original Mint) with agitation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer (loading at 0.30 wt %) | DE after 7 weeks |
|---|---|
| None | 9.78 |
| Compound A | 8.55 |
| Example 3 | 8.17 |
| Example 2 | 7.27 |
| Example 1 | 5.69 |

Compound A is 1-oxyl-2,2,6,6-tetramethyl-4-hydroxypiperidine which is disclosed in WO 2003103622, the publication of U.S. Pat. app. No. 60/377,381, filed May 2, 2002, incorporated herein by reference.

The compounds according to this invention are able to improve clearly the light fastness of mouthwash formulations.

Example 9

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Listerine® Tartar Control Wintermint) with agitation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer (loading at 0.30 wt %) | DE after 4 weeks |
|---|---|
| Compound A | 13.84 |
| Example 1 | 2.24 |
| Example 2 | 2.06 |
| Example 3 | 1.90 |
| Example 5 | 1.85 |

Compound A is 1-oxyl-2,2,6,6-tetramethyl-4-hydroxypiperidine which is disclosed in WO 2003103622, the publication of U.S. Pat. app. No. 60/377,381, filed May 2, 2002, incorporated herein by reference.

The compounds according to this invention are able to improve clearly the light fastness of mouthwash formulations.

Example 10

The instant compounds are added to a commercial shampoo formulation and are evaluated for their ability to reduce the amount of dye fading when the samples are exposed to fluorescent lighting. The instant compounds are dissolved in a shampoo formulation with agitation. 3-(2H-benzotriazol-2-yl)-4-hydroxy-5-(1-methylpropyl)-benzenesulfonic acid monosodium salt, a benzotriazole UV absorber, is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

Example 11

The instant compounds are added to a commercial shampoo formulation and are evaluated for their ability to reduce the amount of dye fading when the samples are exposed to fluorescent lighting. The instant compounds are dissolved in a shampoo formulation with agitation. An s-triazine UV absorber is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

Example 12

The instant compounds are added to a commercial shampoo formulation and are evaluated for their ability to reduce the amount of dye fading when the samples are exposed to fluorescent lighting. The instant compounds are dissolved in a shampoo formulation with agitation. A benzophenone UV absorber is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

Example 13

The instant compounds are added to a commercial mouthwash formulation and are evaluated for their ability to reduce the amount of dye fading when the samples are exposed to fluorescent lighting. The instant compounds are added to a mouthwash formulation with agitation. 3-(2H-benzotriazol-2-yl)-4-hydroxy-5-(1-methylpropyl)-benzenesulfonic acid monosodium salt, a benzotriazole UV absorber, is added to the mouthwash formulation. These formulations are weathered under fluorescent lighting at ambient temperature. The CIEL*a*b coordinates before and after exposure are measured. Color change is expressed as Delta E (DE). The compounds according to this invention are quite efficacious in improving light fastness of mouthwash formulations.

Example 14

The instant compounds are added to a commercial mouthwash formulation and are evaluated for their ability to reduce the amount of dye fading when the samples are exposed to fluorescent lighting. The instant compounds are added to a mouthwash formulation with agitation. An s-triazine UV absorber is added to the mouthwash formulation. These formulations are weathered under fluorescent lighting at ambient temperature. The ClEL*a*b coordinates before and after exposure are measured. Color change is expressed as Delta E (DE). The compounds according to this invention are quite efficacious in improving light fastness of mouthwash formulations.

Example 15

The instant compounds are added to a commercial mouthwash formulation and are evaluated for their ability to reduce the amount of dye fading when the samples are exposed to fluorescent lighting. The instant compounds are added to a mouthwash formulation with agitation. A benzophenone UV absorber is added to the mouthwash formulation. These formulations are weathered under fluorescent lighting at ambient temperature. The ClEL*a*b coordinates before and after exposure are measured. Color change is expressed as Delta E (DE). The compounds according to this invention are quite efficacious in improving light fastness of mouthwash formulations.

Example 16

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR BLUE ABL9 (FD&C Blue No. 1)

About 20 mL of each of the aqueous test formulations are placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 17

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR RED ARE33 (FD&C Red No. 33).

About 20 mL of each of the aqueous test formulations are placed in a borosilicate glass bottle. The glass bottles are exposed in an Atlas Ci-65 Xenon arc WeatherOmeter, AATCC Test Method 16, option E. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 18

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is FD&C Red No. 40.

About 20 mL of each of the aqueous test formulations are placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 19

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR BLUE ABL9 (FD&C Blue No. 1)

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 20

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR RED ARE33 (FD&C Red No. 33).

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 21

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is FD&C Red No. 40.

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

Example 22

The components of phase A are thoroughly mixed in a homogenizer for 10 min at 75-80° C. The water phase B, likewise heated to 75-80° C. beforehand, is slowly added and the mixture is homogenized for 1 min. The mixture is cooled, with stirring, to 40° C. and then phases C and E are added and the mixture is homogenized for 1 min. Subsequently, phase D is added and the mixture is homogenized for ½ min and cooled, with stirring, to room temperature.

| Phase | Ingredients | (w/w) % |
|---|---|---|
| A | passionflower oil | 8 |
| | glyceryl dioleate | 4 |
| | dicapryl ether | 4 |

-continued

| Phase | Ingredients | (w/w) % |
|---|---|---|
| | Isopropylisostearate | 4 |
| | instant stabilizer | 0.05 |
| B | water, demin. | ad. 100 |
| | EDTA | 0.1 |
| C | Carbomer | 0.15 |
| D | sodium hydroxide | 10% |
| | | 0.20 |
| E | perfume; preservative | q.s. |

It is seen that the stabilizers of the present invention provide excellent color stability in personal care products.

Example 23

The components below are thoroughly mixed in the cited sequence at 50° C., a clear homogeneous solution being obtained. The UV absorber is, for example, 3-(2H-benzotriazol-2-yl)-4-hydroxy-5-(1-methylpropyl)-benzenesulfonic acid monosodium salt.

| Ingredients | (w/w) % |
|---|---|
| ethanol, 96% | 60 |
| d-limonene | 5 |
| cedrene | 1.5 |
| citronellol | 0.5 |
| savin | 0.5 |
| instant stabilizer | 0.08 |
| UV absorber | 0.1 |
| S,S-EDDS | 0.005 |
| colorant (D&C Yellow No. 5) | 0.02 |
| water | ad. 100 |

Excellent results are achieved for this example of a toilet water formulation.

Example 24

The hydroxypropyl cellulose is first predissolved in half of the alcohol (Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved. The UV absorber used is, for example, benzophenone-4 is 5-benzoyl-4-hydroxy-2-methoxybenzenesulfonic acid, sodium salt.

| Ingredients | (w/w) % |
|---|---|
| alcohol, anhydrous | 96.21 |
| octylacrylamide/acrylate/butylaminoethylmethacrylate copolymer | 2.52 |
| hydroxypropyl cellulose | 0.51 |
| aminomethylpropanol (95%) | 0.46 |
| instant stabilizer | 0.05 |
| UV absorber | 0.05 |
| perfume oil | 0.20 |

Excellent results are achieved for this example of a hair styling spray formulation.

Example 25

The components listed below are mixed, with stirring, at room temperature until they are completely dissolved. The pH is 6.5. The UV absorber is, for example, 2-(2-hydroxy-3-dodecyl-5-methylphenyl)-2H-benzotriazole.

| Ingredients | (w/w) % |
| --- | --- |
| sodium myreth sulfate | 50.00 |
| TEA abietoyl collagen hydrolysate | 3.50 |
| laureth-3 | 3.00 |
| colorant (D&C Red No. 33) | 0.20 |
| instant stabilizer | 0.05 |
| UV absorber | 0.15 |
| phosphonomethylchitosan, sodium salt | 0.01 |
| perfume oil | 0.10 |
| water | ad. 100 |

Excellent results are achieved for this example of a shampoo composition for oily hair.

Example 26

The stabilizer is predissolved in the terpene. The components are then stirred in the cited sequence at about 65° C. until homogeneous. The mixture is then cooled to room temperature.

| Ingredients | (w/w) % |
| --- | --- |
| synthetic soap (Zetesap 813) | 7.85 |
| Glycerol | 6.00 |
| anionic surfactant (Lumorol 4192; Mulsifan RT 13) | 22.00 |
| Vaseline | 11.00 |
| paraffin 52/54 | 20.00 |
| Talcum | 2.00 |
| orange terpene | 4.00 |
| instant stabilizer | 0.02 |
| Water | 27.13 |

Excellent results are achieved for this example of a leather dressing and cleaning agent composition.

Example 27

The components listed below are dissolved in the cited sequence until a clear homogeneous mixture is obtained.

| Ingredients | (w/w) % |
| --- | --- |
| anionic/amphoteric surfactants (Lumorol RK) | 0.7 |
| butyl glycol | 5.0 |
| Isopropanol | 20.0 |
| d-limonene | 4.00 |
| instant stabilizer | 0.02 |
| water, demin. | ad. 100 |

Excellent results are achieved for this example of a glass detergent formulation.

Example 28

The instant stabilizers are each deposited (from water) on a dyed cotton fabric at 0.05, 0.1, 0.2, 0.5 and 1.0 percent by weight, based on the weight of the cotton. The dyed fabrics contain the following dyes at 0.05, 0.1, 0.2 and 0.5 percent by weight based on cotton. This results in 60 separate formulations for each dye listed:

Scarlet HE-3G

Crimson HE-XL

Yellow HE-6G

Red HE-XL

Blue HE-XL

Turquoise H-A

Navy HE-XL

Remazol

Red RB

Brilliant Red RBS

Orange FR

Navy CG

Turquoise G

Black B

The cotton fabrics are subjected to light exposure in an Atlas Ci-65 Xenon arc WeatherOmeter or to accelerated fluorescent lighting. The present stabilizers provide outstanding color protection to the dyed fabrics. This experiment simulates dye protection achievable through deposition of the present stabilizers via treatment with, for example, stabilizer-containing laundry detergent or fabric conditioner.

Example 29

The instant stabilizers and UV absorbers, for example 3-(2H-benzotriazol-2-yl)-4-hydroxy-5-(1-methylpropyl)-benzenesulfonic acid monosodium salt, are each deposited (from water) on a dyed cotton fabric at 0.05, 0.1, 0.2, 0.5 and 1.0 percent by weight, based on the weight of the cotton. The dyed fabrics contain the following dyes at 0.05, 0.1, 0.2 and 0.5 percent by weight based on cotton. This results in 60 separate formulations for each dye listed:

Scarlet HE-3G

Crimson HE-XL

Yellow HE-6G

Red HE-XL

Blue HE-XL

Turquoise H-A

Navy HE-XL

Remazol

Red RB

Brilliant Red RBS

Orange FR

Navy CG

Turquoise G

Black B

The cotton fabrics are subjected to light exposure in an Atlas Ci-65 Xenon arc WeatherOmeter or to accelerated fluorescent lighting. The present stabilizers provide outstanding color protection to the dyed fabrics. This experiment simulates dye protection achievable through deposition of the present stabilizers via treatment with for example stabilizer-containing laundry detergent or fabric conditioner.

What is claimed is:

1. A stabilized composition comprising (a) a body care product and (b) an effective stabilizing amount of one or more compounds of formula (I)

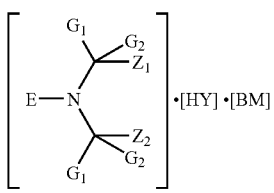

(I)

wherein $G_1$ and $G_2$ are independently alkyl of 1 to 4 carbon atoms or are together pentamethylene; $Z_1$ and $Z_2$ are each methyl, or $Z_1$ and $Z_2$ together form an unsubstituted linking moiety or a linking moiety substituted by one or more groups selected from an ester, ether, hydroxy, oxo, cyanohydrin, amide, amino, carboxy or an urethane group;

E is alkoxy of 1 to 18 carbon atoms, cycloalkoxy of 5 to 12 carbon atoms or aralkoxy of 7 to 15 carbon atoms, or E is —O-T-(OH)$_b$, T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

HY is an inorganic or organic acid; and, wherein the total charge of cations is equal to the total charge of anions; and BM is a basic material selected from the group consisting of alkali metal hydroxides, alkaline earth metal hydroxides, and amines.

2. A stabilized composition according to claim 1 wherein $Z_1$ and $Z_2$ as a linking moiety are a chain of 2 or 3 carbon atoms or 1 or 2 carbon atoms and a nitrogen or oxygen atom forming together with the remaining structure in formula (I) a saturated unsubstituted 5- or 6-membered heterocyclic ring or a 5- or 6-membered heterocyclic ring substituted by one or more groups selected from the group consisting of ester, ether, hydroxy, oxo, cyanohydrin, amide, amino, carboxy, and urethane.

3. A stabilized composition according to claim 1 wherein Y in formula (I) is selected from the group consisting of phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, a carboxylate of hydroxyethyl-ethylenediaminetriacetic acid, a carboxylate of ethylenediaminetetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, and alkyl-substituted arylsulfonate.

4. A stabilized composition according to claim 1 wherein the compounds of formula (I) are selected from the group consisting of formulae (A*) to (EE*) and (III) to (IIIc)

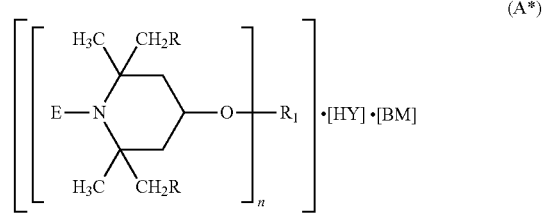

(A*)

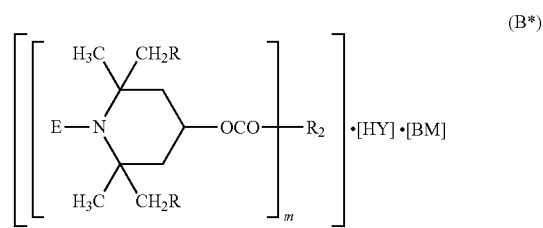

(B*)

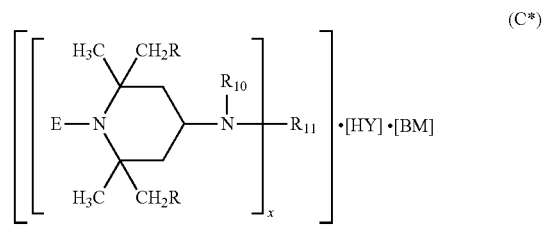

(C*)

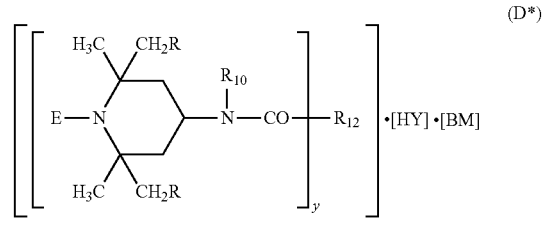

(D*)

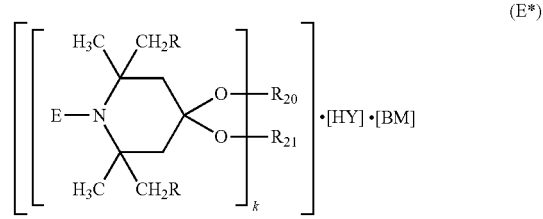

(E*)

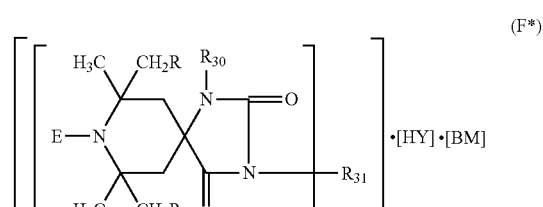

(F*)

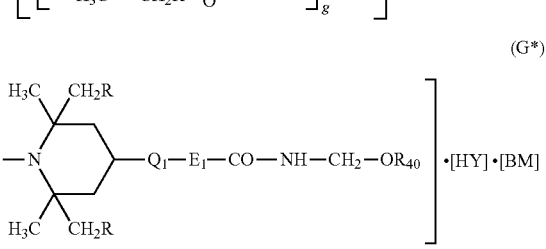

(G*)

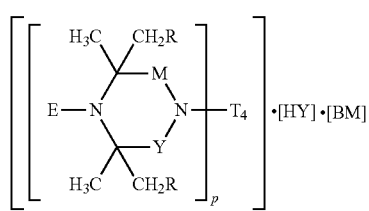 (H*)
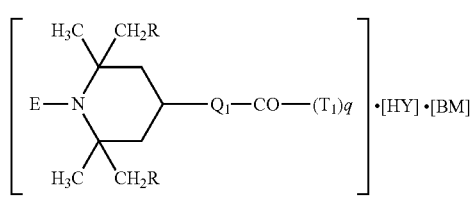 (I*)
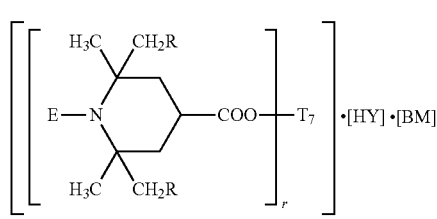 (J*)
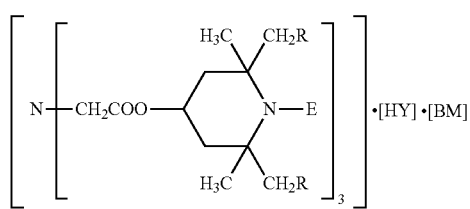 (K*)
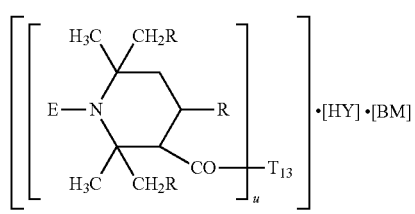 (L*)
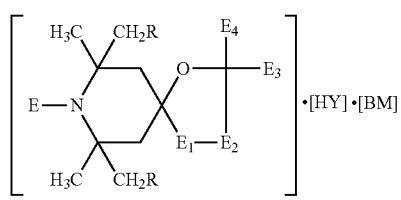 (M*)
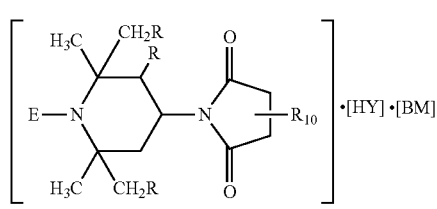 (O*)
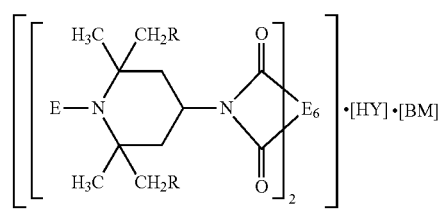 (P*)
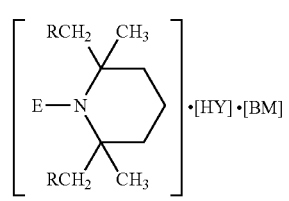 (Q*)
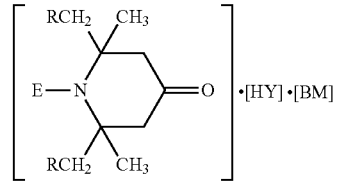 (R*)
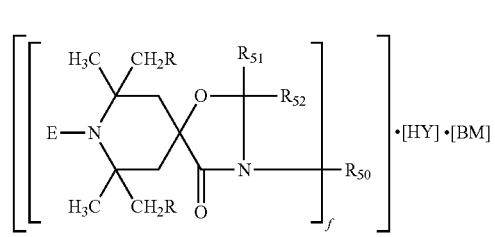 (T*)
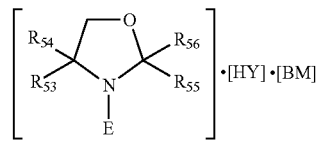 (U*)
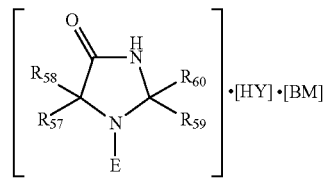 (V*)
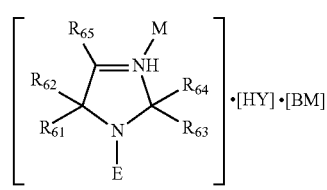 (W*)

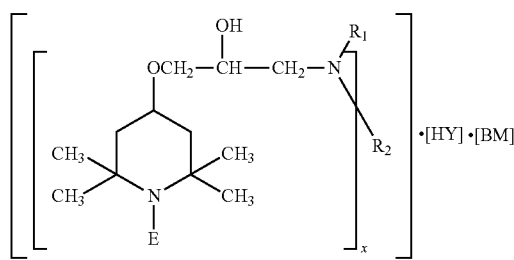
(Y*)

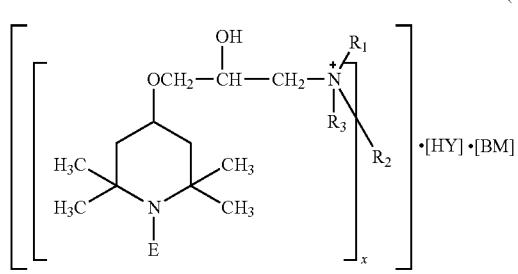
(Z*)

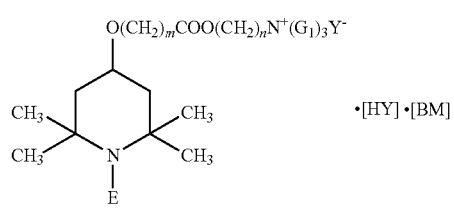
(AA*)

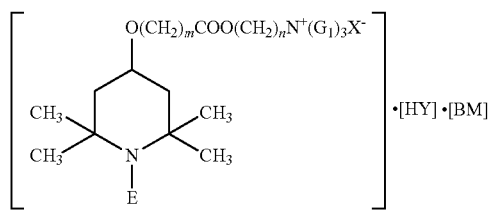
(BB*)

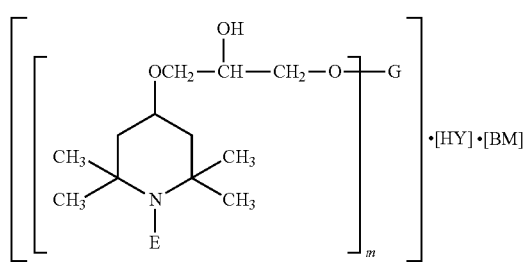
(DD*)

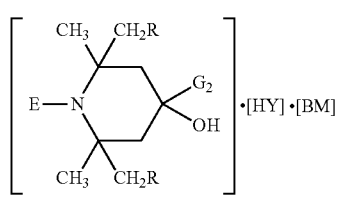
(EE*)

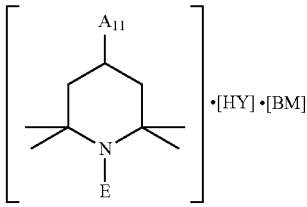
(III)

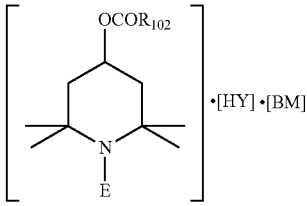
(IIIa)

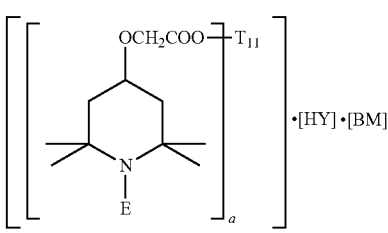
(IIIb)

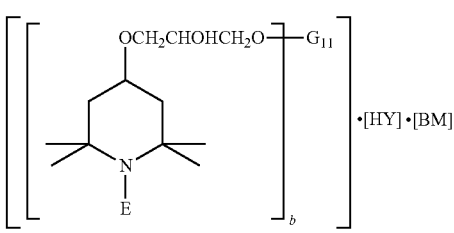
(IIIc)

wherein

E is alkoxy of 1 to 18 carbon atoms, cycloalkoxy of 5 to 12 carbon atoms or aralkoxy of 7 to 15 carbon atoms, or E is —O-T-(OH)$_b$, T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen or methyl; and in formula (A*) n is 1 or 2, when n is 1, $R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is alkyl of 1 to 8 carbon atoms or benzyl, when n is 2, $R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups;

in formula (B*), m is 1 to 4, and when m is 1, $R_2$ is alkyl of 1 to 18 carbon atoms, alkyl of 3 to 18 carbon atoms interrupted by —COO—, alkyl of 3 to 18 carbon atoms substituted by COOH or COO—, or $R_2$ is —$CH_2$($OCH_2CH_2$)$_n$ $OCH_3$ where n is 1 to 12, or $R_2$ is cycloalkyl of 5 to 12 carbon atoms, aryl of 6 to 12 carbon atoms, or said aryl substituted by one to four alkyl groups of 1 to 4 carbon atoms, or $R_2$ is —$NHR_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —$N(R_3)_2$ where $R_3$ is as defined above, when m is 2, $R_2$ is alkylene of 1 to 12 carbon atoms, alkenylene of 4 to 12 carbon atoms, xylylene, alkylene of 2 to 12 carbon atoms interrupted by —COO—, alkylene of 3 to 18 carbon atoms substituted by COOH or COO—, or $R_2$ is —$CH_2$($OCH_2CH_2$)$_n$ $OCH_2$— where n is 1 to 12, or $R_2$ is cycloalkylene of 5 to 12 carbon atoms, aralkylene of 7 to 15 carbon atoms or arylene of 6 to 12 carbon atoms, or $R_2$ is —$NHR_4NH$— where $R_4$ is alkylene of 2 to 18 carbon atoms, cycloalkylene of 5 to 12 carbon atoms, aralkylene of 8 to 15 carbon atoms or arylene of 6 to 12 carbon atoms, or $R_2$ is —$N(R_3)R_4N(R_3)$— where $R_3$ and $R_4$ are as defined above, or $R_2$ is —CO—, —NH—CO—NH—, or —N(R3)-CO—N(R3)-, when m is 3, $R_2$ is alkanetriyl of 3 to 8 carbon atoms or benzenetriyl, or when m is 4, $R_2$ is alkanetetrayl of 5 to 8 carbon atoms or benzenetetrayl, in formula (C*), $R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, x is 1 or 2, and when x is 1, $R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is hydrogen, alkyl of 1 to 8 carbon atoms or benzyl, or when x is 2, $R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula (D*), y is 1 to 4, $R_{10}$ is as defined above, and $R_{12}$ is defined as $R_2$ above, in formula (E*), k is 1 or 2, when k is 1, $R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or $R_{20}$ and $R_{21}$ together are alkylene of 2 to 8 carbon atoms or said alkylene substituted by hydroxyl, or are acyloxy-alkylene of 4 to 22 carbon atoms, or when k is 2, $R_{20}$ and $R_{21}$ are together (—$CH_2$)$_2$C($CH_2$—)$_2$, in formula (F*), $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, when g is 2, $R_{31}$ is defined as $R_1$ above when n is 2, in formula (G*), $Q_1$ is —$NR_{41}$— or —O—, $E_1$ is alkylene of 1 to 3 carbon atoms, or $E_1$ is —$CH_2$—CH($R_{42}$)—O— where $R_{42}$ is hydrogen, methyl or phenyl, or $E_1$ is —($CH_2$)$_3$—NH— or $E_1$ is a direct bond, $R_{40}$ is hydrogen or alkyl of 1 to 18 carbon atoms, $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —$CH_2$—CH($R_{42}$)—OH where $R_{42}$ is as defined above, in formula (H*), p is 1 or 2, $T_4$ is as defined for $R_{11}$ when x is 1 or 2, M and Y are independently methylene or carbonyl, preferably M is methylene and Y is carbonyl, in formula (I*), this formula denotes a recurring structural unit of a polymer where $T_1$ is ethylene or 1,2-propylene or is the repeating structural unit derived from an alpha-olefin copolymer with an alkyl acrylate or methacrylate, and where q is 2 to 100, $Q_1$ is —$N(R_{41})$— or —O— where $R_{41}$ is as defined above, in formula (J*), r is 1 or 2, $T_7$ is as defined for $R_1$ when n is 1 or 2 in formula (A*), preferably $T_7$ is octamethylene when r is 2, in formula (L*), u is 1 or 2, $T_{13}$ is as defined for $R_1$ when n is 1 or 2 in formula (A*), with the proviso that $T_{13}$ is not hydrogen when u is 1, in formula (M*), $E_1$ and $E_2$, being different, each are —CO— or —N($E_5$)-where $E_5$ is hydrogen, alkyl of 1 to 12 carbon atoms or alkoxycarbonylalkyl of 4 to 22 carbon atoms, preferably $E_1$ is —CO— and $E_2$ is —N($E_5$)-, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, preferably methyl, in formula (O*), $R_{10}$ is as defined for $R_{10}$ in formula (C*), in formula (P*), $E_6$ is an aliphatic or aromatic tetravalent radical, preferably neopentanetetrayl or benzenetetrayl, in formula (T*),
$R_{51}$ is hydrogen, alkyl of 1 to 18 carbon atoms, cycloalkyl of 5 to 12 carbon atoms, or aryl of 6 to 10 carbon atoms,
$R_{52}$ is hydrogen or alkyl of 1 to 18 carbon atoms, or
$R_{51}$ and $R_{52}$ together of alkylene of 4 to 8 carbon atoms,
f is 1 or 2,
when f is 1,
$R_{50}$ is as defined for $R_{11}$ in formula (C*) when x is 1, or $R_{50}$ is —$(CH_2)_z COOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl,
when f is 2,
$R_{50}$ is as defined for $R_{11}$ in formula (C*) when x is 2,
in formula (U*),
$R_{53}$, $R_{54}$, $R_{55}$ and $R_{56}$ are independently alkyl of 1 to 4 carbon atoms or are together pentamethylene,
in formula (V*),
$R_{57}$, $R_{58}$, $R_{59}$ and $R_{60}$ are independently alkyl of 1 to 4 carbon atoms or are together pentamethylene,
in formula (W*),
$R_{61}$, $R_{62}$, $R_{63}$ and $R_{64}$ are independently alkyl of 1 to 4 carbon atoms or are together pentamethylene,
$R_{65}$ is alkyl of 1 to 5 carbon atoms,
M is hydrogen or oxygen,
wherein in formulas (Y*) to (BB*),
n is 2 to 3,
$G_1$ is hydrogen, methyl, ethyl, butyl or benzyl,
m is 1 to 4,
x is 1 to 4,
when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen,
or $R_1$ and $R_2$ are together tetramethylene, pentamethylene, hexamethylene or 3-oxapentamethylene,
when x is 2,
$R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group,
$R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups;
o-, m- or p-phenylene or said phenylene substituted by one or two alkyl of 1 to 4 carbon atoms, or
$R_2$ is —$(CH_2)_k O[(CH_2)_k O]_h (CH_2)_k$— where k is 2 to 4 and h is 1 to 40, or
$R_1$ and $R_2$ together with the two N atoms to which they are attached are piperazin-1,4-diyl,
when x is 3,
$R_1$ is hydrogen,
$R_2$ is alkylene of 4 to 8 carbon atoms interrupted by one nitrogen atom,
when x is 4,
$R_1$ is hydrogen,
$R_2$ is alkylene of 6 to 12 carbon atoms interrupted by two nitrogen atoms,
$R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group,
p is 2 or 3,
in formula (DD*),
m is 2 or 3,
when m is 2,
G is —$(CH_2CHR—O)_r CH_2CHR$—, where r is 0 to 3, and R is hydrogen or methyl, and
when m is 3, G is glyceryl,
in formula (EE*),
$G_2$ is —CN, —$CONH_2$ or —$COOG_3$ where $G_3$ is hydrogen, alkyl of 1 to 18 carbon atoms or phenyl, in formulae (III) to (IIIc)
A11 is $OR_{101}$ or $NR_{111}R_{112}$,
$R_{101}$ is alkenyl of 2 to 4 carbon atoms, propargyl, glycidyl, alkyl of 2 to 6 carbon atoms interrupted by one or two oxygen atoms, substituted by one to three hydroxyl groups or both interrupted by said oxygen atoms and substituted by said hydroxyl groups, or $R_{101}$ is alkyl of 1 to 4 carbon atoms substituted by carboxy or by the alkali metal, ammonium or $C_1$-$C_4$alkylammonium salts thereof; or $R_{101}$ is alkyl substituted by $COOE_{10}$ where $E_{10}$ is methyl or ethyl,
$R_{102}$ is alkyl of 3 to 5 carbon atoms interrupted by —COO— or by —CO—, or $R_{102}$ is —$CH_2(OCH_2CH_2)_c COCH_3$ where c is 1 to 4; or
$R_{102}$ is —$NHR_{103}$ where $R_{103}$ is alkyl of 1 to 4 carbon atoms,
a is 2 to 4,
when a is 2,
$T_{11}$ is —$(CH_2CHR_{100}—O)_d CH_2CHR_{100}$—, where d is 0 or 1, and $R_{100}$ is hydrogen or methyl,
when a is 3, $T_{11}$ is glyceryl,
when a is 4, $T_{11}$ is neopentanetetrayl,
b is 2 or 3,
when b is 2,
$G_{11}$ is —$(CH_2CHR_{100})_d CH_2CHR_{100}$—, where d is 0 or 1, and $R_{100}$ is hydrogen or methyl, and
when b is 3, $G_{11}$ is glyceryl;
$R_{111}$ is hydrogen, unsubstituted alkyl of 1 to 4 carbon atoms, alkyl of 1 to 4 carbon atoms substituted by one or two hydroxyl, alkyl of 1 to 4 carbon atoms interrupted by one or two oxygen atoms, or both substituted by one hydroxyl and interrupted by one or two oxygen atoms,
$R_{112}$ is —CO—$R_{113}$ where $R_{113}$ has the same meaning as $R_{111}$, or $R_{113}$ is $NHR_{114}$, wherein $R_{114}$ is unsubstituted alkyl of 1 to 4 carbon atoms, alkyl of 1 to 4 carbon atoms substituted by one or two hydroxyl, alkyl of 1 to 4 carbon atoms substituted by alkoxy of 1 to 2 carbon atoms, or both substituted by one hydroxyl and by alkoxy of 1 to 2 carbon atoms, or
$R_{111}$ and $R_{112}$ together are —CO—$CH_2CH_2$—CO—, or $(CH_2)_6 CO$—;
BM is a basic material selected from the group consisting of alkali metal hydroxides, alkaline earth metal hydroxides, and amines;
amines are $R_{115}$—$N(R_{116})$—$R_{117}$, wherein
$R_{115}$, $R_{116}$, and $R_{117}$ are independently hydrogen, straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{118}$, —$OR_{119}$, $R_1$, or —$NH_2$ groups or mixtures thereof; or said alkyl or said alkenyl interrupted by one or more —O—, —NH— or —$NR_{119}$— groups or mixtures thereof and which can be unsubstituted or substituted by one or more —OH, —$OR_{119}$ or —$NH_2$ groups or mixtures thereof;

$R_{118}$ is hydrogen, straight or branched chain $C_1$-$C_{18}$alkyl, $C_5$-$C_{12}$cycloalkyl, straight or branched chain $C_3$-$C_8$alkenyl, $C_6$-$C_{14}$aryl or $C_7$-$C_{15}$aralkyl, $R_{119}$ is straight or branched chain alkyl of 1 to 18 carbon atoms;

alkali metal hydroxide is sodium hydroxide, potassium hydroxide, or rubidium hydroxide;

alkaline earth metal hydroxide is magnesium hydroxide, calcium hydroxide, strontium hydroxide, or barium hydroxide;

HY is an inorganic or organic acid; wherein the total charge of cations is equal to the total charge of anions; and Y is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, a carboxylate of hydroxyethylethylenediamine-triacetic acid, a carboxylate of ethylenediaminetetraacetic acid, a carboxylate of diethylenetriamine-pentaacetic acid, a carboxylate of diethylenediaminetetraacetic acid, a carboxylate of diethylene-triaminepentaacetic acid, alkylsulfonate, arylsulfonate, or alkyl-substituted arylsulfonate.

5. A stabilized composition according to claim 4 wherein the compounds of formula (I) are selected from the group consisting of (A*), (B*), (C*), (D*), (Q*), (R*), (Y*), and (Z*), wherein E is alkoxy of 1 to 10 carbon atoms, cycloalkoxy of 5 to 8 carbon atoms or aralkoxy of 7 to 12 carbon atoms, or E is —O-T-(OH)$_b$, T is a straight or branched chain alkylene of 1 to 10 carbon atoms, cycloalkylene of 5 to 10 carbon atoms, cycloalkenylene of 5 to 10 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen;

in formula (A*), n is 1 or 2, when n is 1, $R_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen or alkyl of 1 to 4 carbon atoms, when n is 2, $R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups, in formula (B*), m is 1 or 2 when m is 1, $R_2$ is alkyl of 1 to 4 carbon atoms or $R_2$ is $CH_2(OCH_2CH_2)_n$ $OCH_3$ where n is 1 to 12, or $R_2$ is phenyl, or said phenyl substituted by one to three methyl groups, or $R_2$ is —NHR$_3$ where R$_3$ is alkyl of 1 to 4 carbon atoms or phenyl, or said phenyl substituted by one or two methyl groups, when m is 2, $R_2$ is alkylene of 1 to 8 carbon atoms, alkenylene of 4 to 8 carbon atoms, or $R_2$ is —$CH_2(OCH_2CH_2)_nOCH_2$— where n is 1 to 12, or $R_2$ is —NHR$_4$NH— where $R_4$ is of 2 to 6 carbon atoms, aralkylene of 8 to 15 carbon atoms or arylene of 6 to 12 carbon atoms, or $R_2$ is —CO— or —NHCONH—, in formula (C*), $R_{10}$ is hydrogen or, alkanoyl of 1 to 3 carbon atoms, x is 1 or 2, when x is 1, $R_{11}$ is hydrogen, alkyl of 1 to 6 carbon atoms or glycidyl, or $R_{11}$ is alkyl of 1 to 4 carbon atoms substituted by a carboxy group or by COOZ where Z is hydrogen or alkyl of 1 to 4 carbon atoms, when x is 2, $R_{11}$ is alkylene of 1 to 6 carbon atoms, in formula (D*), $R_{10}$ is hydrogen, y is 1 or 2, $R_{12}$ is defined as $R_2$ above, in formula (Y*) and (Z*), x is 1 or 2, when x is 1, $R_1$ and $R_2$ are independently alkyl of 1 to 4 carbon atoms or $R_1$ and $R_2$ are together tetramethylene, or pentamethylene, $R_2$ is hydrogen or alkyl of 1 to 4 carbon atoms, said alkyl group substituted by a hydroxyl group, when x is 2, $R_1$ is hydrogen, alkyl of 1 to 4 carbon atoms, said alkyl substituted by a hydroxyl group, $R_2$ is alkylene of 2 to 6 carbon atoms, $R_3$ is as defined above, BM is a basic material selected from the group consisting of alkali metal hydroxides, alkaline earth metal hydroxides, and amines;

amines are $R_{115}$—N($R_{116}$)—$R_{117}$, wherein $R_{115}$, $R_{116}$, and $R_{117}$ are independently hydrogen, straight or branched alkyl chain of 1 to 18 carbon atoms, straight or branched chain alkenyl of 2 to 12 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OR$_{119}$, or —NH$_2$ groups or mixtures thereof; or said alkyl or said alkenyl interrupted by one or more —O—, —NH— or —NR$_{119}$— groups or mixtures thereof and which can be unsubstituted or substituted by one or more —OH, —OR$_{119}$ or —NH$_2$ groups or mixtures thereof;

alkali metal hydroxide is sodium hydroxide or potassium hydroxide;

alkaline earth metal hydroxide is magnesium hydroxide and calcium hydroxide;

HY is an inorganic or organic acid; and, wherein the total charge of cations is equal to the total charge of anions; and Y is phosphate, phosphonate, carbonate, bicarbonate, chloride, bromide, bisulfate, sulfate, borate, formate, acetate, benzoate, citrate, oxalate, tartrate, acrylate, fumarate, maleate, itaconate, glycolate, gluconate, malate, mandelate, tiglate, ascorbate, a carboxylate of nitrilotriacetic acid, a carboxylate of hydroxyethylylenediaminetriacetic acid, a carboxylate of ethylenediaminetetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

6. A stabilized composition according to claim 5 wherein the compounds of formula (I) are selected from the group consisting of (A*), (B*), (C*), (D*), (Q*), and (R*),
wherein
E is alkoxy of 1 to 10 carbon atoms, cycloalkoxy of 5 to 8 carbon atoms or aralkoxy of 7 to 12 carbon atoms, or E is —O-T-(OH)$_b$,
T is a straight or branched chain alkylene of 1 to 10 carbon atoms, cycloalkylene of 5 to 10 carbon atoms, cycloalkenylene of 5 to 10 carbon atoms, a straight or branched chain alkylene of 1 to 4 carbon atoms substituted by phenyl or by phenyl substituted by one or two alkyl groups of 1 to 4 carbon atoms;
b is 1, 2 or 3 with the proviso that b cannot exceed the number of carbon atoms in T, and when b is 2 or 3, each hydroxyl group is attached to a different carbon atoms of T;
R is hydrogen,
in formula (A*),
h is 1,
$R_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
$R_1$ is alkyl of 1 to 4 carbon atoms substituted by —COOZ where Z is hydrogen or alkyl of 1 to 4 carbon atoms,
in formula (B*),
m is 1 or 2,
$R_2$ is alkyl of 1 to 4 carbon atoms or $R_2$ is $CH_2(OCH_2CH_2)_n OCH_3$ where n is 1 to 4,
when m is 2,
$R_2$ is alkylene of 1 to 8 carbon atoms,
in formula (C*),
$R_{10}$ is hydrogen or alkanoyl of 1 or 2 carbon atoms,
x is 1 or 2,
when x is 1,
$R_{11}$ is hydrogen, alkyl of 1 to 4 carbon atoms or glycidyl,
$R_{11}$ is alkyl of 1 to 4 carbon atoms substituted by COOZ where Z is hydrogen or alkyl of 1 to 4 carbon atoms,
when x is 2,
$R_{11}$ is alkylene of 1 to 6 carbon atoms,
in formula (D*),
$R_{10}$ is hydrogen,
y is 1 or 2,
$R_{12}$ is defined as $R_2$ above;
BM is a basic material selected from the group consisting of alkali metal hydroxides, alkaline earth metal hydroxides, and amines;
amines are $R_{115}$—N($R_{116}$)—$R_{117}$, wherein
$R_{115}$, $R_{116}$, and $R_{117}$ are independently hydrogen, straight or branched alkyl chain of 1 to 12 carbon atoms, or said alkyl substituted by one or more —OH, —OR$_{119}$, or —NH$_2$ groups or mixtures thereof; or said alkyl interrupted by one or more —O—, —NH— or —NR$_{119}$— groups or mixtures thereof and which can be unsubstituted or substituted by one or more —OH, —OR$_{119}$ or —NH$_2$ groups or mixtures thereof;
$R_{119}$ is straight or branched chain alkyl of 1 to 8 carbon atoms;
alkali metal hydroxide is sodium hydroxide or potassium hydroxide;
alkaline earth metal hydroxide is calcium hydroxide;
HY is an inorganic or organic acid; and, wherein the total charge of cations is equal to the total charge of anions; and
Y is phosphate, phosphonate, carbonate, bicarbonate, chloride, bromide, bisulfate, sulfate, borate, formate, acetate, benzoate, citrate, oxalate, tartrate, ascorbate, acrylate, fumarate, maleate, itaconate, glycolate, gluconate, malate, mandelate, tiglate, a carboxylate of nitrilotriacetic acid, a carboxylate of hydroxyethylethylenediaminetriacetic acid, a carboxylate of ethylenediaminetetraacetic acid, a carboxylate of diethylenetriaminepentaacetic acid, a carboxylate of diethylenediaminetetraacetic acid, a carboxylate of diethylenetriaminepentaacetic acid, alkylsulfonate, arylsulfonate, or alkyl-substituted arylsulfonate.

7. A stabilized composition according to claim 1 wherein the compound of formula (I) is selected from the group consisting of
(a) Monosodium 1-methoxy-2,2,6,6-tetramethyl-4-acetoxypiperidinium citrate;
(b) Monopotassium 1-methoxy-2,2,6,6-tetramethyl-4-acetamidopiperidinium phosphate;
(c) Monoammonium 1-butoxy-2,2,6,6-tetramethyl-4-acetamidopiperidinium sulfate;
(d) Mono-(N,N,N-triethylammonium)1-phenoxy-2,2,6,6-tetramethyl-4-methoxy-piperidinium tartrate;
(e) Mono-[N,N-di-n-butyl ammonium]1-ethoxy-2,2,6,6-tetramethyl-4-acetoxypiperidinium maleate;
(f) Mono-[N,N,N-(2-hydroxyethyl)ammonium]1-methoxy-2,2,6,6-tetramethyl-4-propoxy-piperidinium oxalate;
(g) Monosodium 1-methoxy-2,2,6,6-tetramethyl-4-(2-hydroxy-4-oxapentoxy)piperidinium carbonate;
(h) Dipotassium 1-(2-hydroxy-2-methylpropoxy)-2,2,6,6-tetramethyl-4-hydroxypiperidinium citrate;
(i) Monosodium bis(1-(2-hydroxy-2-methylpropoxy)-2,2,6,6-tetramethyl-4-hydroxypiperidinium) citrate;
(j) Diammonium (1-(2-hydroxy-2-methylpropoxy)-2,2,6,6-tetramethyl-4-hydroxypiperidinium)citrate;
(k) Monopotassium monosodium bis(1-(2-hydroxy-2-methylpropoxy)-2,2,6,6-tetramethyl-4-hydroxypiperidinium) ethylenediaminetetraacetate;
(l) Monosodium tris(1-(2-hydroxy-2-methylpropoxy)-2,2,6,6-tetramethyl-4-acetamidopiperidinium) ethylenediaminetetraacetate;
(m) Monocalcium bis(1-(2-hydroxy-2-methylpropoxy)-2,2,6,6-tetramethyl-4-oxopiperidinium) ethylenediaminetetraacetate;
(n) Monoammonium tetra(1-(2-hydroxy-2-methylpropoxy)-2,2,6,6-tetramethyl-4-hydroxypiperidinium) diethylenetriaminepentaacetate;
(o) Disodium tris(1-(2-hydroxy-2-methylpropoxy)-2,2,6,6-tetramethyl-4-acetamidopiperidinium) diethylenetriaminepentaacetate;
(p) Tripotassium di(1-(2-hydroxy-2-methylpropoxy)-2,2,6,6-tetramethyl-4-oxopiperidinium) diethylenetriaminepentaacetate;
(q) Monobenzylammonium bis(1-(2-hydroxy-2-methylpropoxy)-2,2,6,6-tetramethyl-4-hydroxypiperidinium) nitrilotriacetate;
(r) Di-[N,N-diethylammonium]mono(1-(2-hydroxy-2-methylpropoxy)-2,2,6,6-tetramethyl-4-acetamidopiperidinium) nitrilotriacetate;
(s) Monosodium bis(1-(2-hydroxy-2-methylpropoxy)-2,2,6,6-tetramethyl-4-oxopiperidinium) nitrilotriacetate;

(t) Diammonium tris(1-(2-hydroxy-2-methylpropoxy)-2,2,6,6-tetramethyl-4-hydroxypiperidinium) diethylenetriaminepentamethylenephosphonate;
(u) Monosodium tetra(1-(2-hydroxy-2-methylpropoxy)-2,2,6,6-tetramethyl-4-acetamidopiperidinium) diethylenetriaminepentamethylenephosphonate; and,
(v) Tripotassium bis(1-(2-hydroxy-2-methylpropoxy)-2,2,6,6-tetramethyl-4-oxopiperidinium) diethylenetriaminepentamethylenephosphonate.

8. A stabilized composition according to claim 7 wherein the compound of formula (I) is selected from the group consisting of
(a) Mono-[N,N,N',N'-tetramethylethylenediammonium]-mono-[1-(2-hydroxy-2-methylpropoxy)-2,2,6,6-tetramethyl-4-hydroxypiperidinium citrate;
(b) Mono-[N,N,N-(2-hydroxyethyl)ammonium]-mono-[1-(2-hydroxy-2-methylpropoxy)-2,2,6,6-tetramethyl-4-propoxy-piperidinium citrate;
(c) Monopotassium tris1-(2-hydroxy-2-methylpropoxy)-2,2,6,6-tetramethyl-4-hydroxypiperidinium citrate; and,
(d) Monosodium bis(1-(2-hydroxy-2-methylpropoxy)-2,2,6,6-tetramethyl-4-hydroxypiperidinium) citrate.

9. A composition according to claim 1 further comprising
(c) one or more compounds selected from the group consisting of the ultraviolet light absorbers, antioxidants, tocopherol, tocopherol acetate, hindered amine light stabilizers, complex formers, optical brighteners, surfactants, and polyorganosiloxanes.

10. A composition according to claim 9 where the ultraviolet light absorbers are selected from the group consisting of the 2H-benzotriazoles, the s-triazines, the benzophenones, the alpha-cyanoacrylates, the oxanilides, the benzoxazinones, the benzoates, and the alpha-alkyl cinnamates.

11. A composition according to claim 1 further comprising
(d) a dye.

12. A composition according to claim 1 where the compounds of component (b) are present in the body care or household products in a concentration of about 5 to about 10000 ppm based on the total formulation by weight.

13. A composition according to claim 12 where the compounds of component (b) are present in a concentration of about 10 to about 5000 ppm based on the total formulation by weight.

14. A composition according to claim 1 wherein the body care product is selected from the group consisting of skin-care products, bath and shower products, liquid soaps, bar soaps, preparations containing fragrances and odoriferous substances, hair-care products, dentifrices, deodorizing and antiperspirant preparations, decorative preparations, light protection formulations, and preparations containing active ingredients.

15. A composition according to claim 14 wherein the skin-care products are selected from the group consisting of body oils, body lotions, body gels, treatment creams, skin protection ointments, shaving preparations, and skin powders.

16. A composition according to claim 14 wherein the preparations containing fragrances and olfactory substances are selected from the group consisting of scents, perfumes, toilet waters, and shaving lotions.

17. A composition according to claim 14 wherein the hair-care products are selected from the group consisting of shampoos, hair conditioners, 2 in 1 conditioners, leave in and rinse off conditioners, agents for styling and treating hair, perming agents, relaxants, hair sprays and lacquers, hair dyeing systems, permanent, demi-permanent, semi-permanent and temporary hair dyeing systems, and hair bleaching agents.

18. A composition according to claim 14 wherein the decorative preparations are selected from the group consisting of lipsticks, nail varnishes, eye shadows, mascaras, dry and moist make-up, rouge, powders, depilatory agents, sun care, and after sun products.

19. A composition according to claim 14 wherein the preparations containing active ingredients are selected from the group consisting of hormone preparations, vitamin preparations, vegetable extract preparations, and antibacterial preparations.

20. A method of stabilizing a body care product, which comprises incorporating therein or applying thereto one or more compounds of the formulae (III) to (IIIc) according to claim 4.

21. A method of stabilizing a body care product, which comprises incorporating therein or applying thereto one or more compounds of the formulae A* to EE* according to claim 4.

22. A method of stabilizing a body care product, each of which contain a dye, which comprises incorporating therein or applying thereto one or more compounds of the formulae (III) to (IIIc) according to claim 4.

23. A method of stabilizing a body care product, each of which contain a dye, which comprises incorporating therein or applying thereto one or more compounds of the formulae A* to EE* according to claim 4.

* * * * *